(12) United States Patent
Moriuchi et al.

(10) Patent No.: US 7,618,445 B2
(45) Date of Patent: Nov. 17, 2009

(54) FLEXIBLE STENT

(75) Inventors: Yousuke Moriuchi, Fujinomiya (JP); Hideaki Yamashita, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 331 days.

(21) Appl. No.: 11/392,490

(22) Filed: Mar. 30, 2006

(65) Prior Publication Data
US 2006/0253187 A1    Nov. 9, 2006

(30) Foreign Application Priority Data
Nov. 4, 2004   (JP)   ............................ 2005-320362
Mar. 30, 2005  (JP)   ............................ 2005-100194

(51) Int. Cl.
*A61F 2/06* (2006.01)
*A61F 2/86* (2006.01)

(52) U.S. Cl. ...................... 623/1.15; 623/1.1; 623/1.17; 623/1.34

(58) Field of Classification Search ................ 623/1.15, 623/1.42, 1.16, 1.17, 1.2
See application file for complete search history.

(56) References Cited

U.S. PATENT DOCUMENTS

| | | | |
|---|---|---|---|
| 5,810,872 A * | 9/1998 | Kanesaka et al. | 623/1.15 |
| 6,013,854 A | 1/2000 | Moriuchi | |
| 6,506,211 B1 | 1/2003 | Skubitz et al. | |
| 6,579,310 B1 * | 6/2003 | Cox et al. | 623/1.16 |
| 6,620,201 B1 | 9/2003 | Nadal et al. | |
| 2003/0105513 A1 * | 6/2003 | Moriuchi et al. | 623/1.15 |
| 2003/0144729 A1 | 7/2003 | Bicek et al. | |
| 2004/0093073 A1 * | 5/2004 | Lowe et al. | 623/1.15 |
| 2004/0243216 A1 | 12/2004 | Gregorich | |

FOREIGN PATENT DOCUMENTS

EP    1 415 616 A1    5/2004

(Continued)

OTHER PUBLICATIONS

European Search Report.

*Primary Examiner*—Thomas J Sweet
*Assistant Examiner*—Yashita Sharma
(74) *Attorney, Agent, or Firm*—Buchanan Ingersoll & Rooney PC

(57) ABSTRACT

A stent (1) to be implanted in an organism includes a plurality of wavy annular members (2) arranged in an axial direction thereof. Each of the wavy annular members (2) has a plurality of one-end side bent portions each having an apex (2*a*) at a one-end side of the stent (1) in the axial direction thereof and a plurality of other-end side bent portions each having an apex (2*b*) at an other-end side of the stent (1) in the axial direction thereof. In the wavy annular members disposed adjacently to each other in the axial direction of the stent, the wavy annular members (2) disposed at the one-end side of the stent in the axial direction thereof has a sharing linear portion (21) having a start point (22) at the apex (2*b*) of one of the other-end side bent portions thereof or in the vicinity of the apex (2*b*) and a termination point (23) between the apex (2*b*) of the other-end side bent portion thereof and the apex (2*a*) of one of the one-end side bent portions thereof. The sharing linear portion (21) integrates the adjacent wavy annular members with each other.

23 Claims, 21 Drawing Sheets

FOREIGN PATENT DOCUMENTS

| | | |
|---|---|---|
| WO | WO 96/26689 A1 | 9/1996 |
| WO | WO 97/32546 A1 | 9/1997 |
| WO | WO 98/30173 A1 | 7/1998 |
| WO | WO 99/65421 A2 | 12/1999 |
| WO | WO 03/082154 A2 | 10/2003 |

* cited by examiner

FLEXIBLE STENT

BACKGROUND OF THE INVENTION

The present invention relates to a stent that is implanted in lumens of an organism such as a blood vessel, the bile duct the trachea, the esophagus, the ureter, and the like to cure a stenosed portion or a closed portion generated in the lumens.

To cure various diseases that are caused when blood vessels or lumens are stenosed or closed, the stent which is a tubular medical appliance is implanted at the stenosed portion or the closed portion to expand them and secure the lumen thereof. When the stent is inserted into the body from the outside, it has a small diameter. The stent is expanded (or restored to its original state) to make its diameter large at the stenosed portion or the closed portion to keep the expanded state of the lumen thereof. The stent is classified into a self-expandable stent and a balloon expandable stent in dependence on the function thereof and an expansion mode. The balloon expandable stent itself has no expanding function. After it is inserted into a desired portion inside the organism, it is secured at the desired portion. Then, a balloon disposed in the stent is inflated to expand (plastically deform) the stent by an expansive force of the balloon so that the stent is brought into close contact with the inner surface of the desired lumen.

It is necessary to perform an operation of expanding the stent of this type in implanting it to the desired portion of the organism. The self-expandable stent is made of an elastic material. The final size of the self-expandable stent is set when it is expanded. In introducing the self-expandable stent into the human body, it is folded into a small size and put into a member (plastic tube in most cases) restricting its configuration. Then the member, namely, the tube is introduced into the human body. The self-expandable stent is discharged from the tube at the desired portion. The self-expandable stent dilates itself owing to its elasticity.

The recent self-expandable stents are mostly composed of annular members formed by connecting a plurality of columnar portions to each other with a plurality of loops so that the annular members have an approximately zigzag pattern. The annular members are connected to each other with connection portions to form the self-expandable stent substantially cylindrically.

In the stent disclosed in WO96/26689, the wavy annular members are connected to each other by connectors obliquely formed.

Another type of stent is known in which adjacent snaking elements or apexes of adjacent zigzag elements penetrate into the adjacent snaking elements or the zigzag elements. This type of the stent is disclosed in WO97/32546. The stent disclosed in WO99/65421, apexes of the above-described zigzag elements are connected to each other with connectors parallel with the axis of the stent.

Still another type of stent is known in which the snaking elements or the zigzag elements form not a straight loop (loops) but a spiral (spirals). The stent of this type is composed of one or a plurality of spirals from its distal end to its proximal end. For example, the stent disclosed in WO98/30173, to keep the configuration of the stent the zigzag elements are connected to each other by connectors parallel with the axis of the stent. The stent disclosed in U.S. Pat. No. 6,013,854 is composed not of wavy annular members but of a plurality of spirals.

The connector is used in all of the above-described conventional stents to connect the elements to each other. The connector is used to connect the elements to each other, but does not contribute to the generation of an expansive force of the stent.

As a result of energetic researches of the present inventors, they have found that a construction which is composed of an element contributing to the generation of the expansive force and which has the operation of the connector allows the stent to keep an expansive force constant or more than a required degree and a favorable coverage.

It is an object of the present invention to provide a stent which does not substantially display an expansive force, does not have a connection portion having a possibility of adversely affecting the performance of the stent when the stent is curved, and has a sufficient and uniform expansive force.

SUMMARY OF THE INVENTION

The object described above is attained by the following a stent.

A stent comprises a plurality of wavy annular members arranged in an axial direction thereof, wherein each of said wavy annular members has a plurality of one-end side bent portions each having an apex at a one-end side of said stent in said axial direction thereof and a plurality of other-end side bent portions each having an apex at an other-end side of said stent in said axial direction thereof; and in said wavy annular members disposed adjacently to each other in said axial direction of said stent, said wavy annular member disposed at said one-end side of said stent in said axial direction thereof has a sharing linear portion having a start point at said apex of one of said other-end side bent portions thereof or in the vicinity of said apex and a termination point between said apex of said other-end side bent portion thereof and said apex of one of said one-end side bent portions thereof; and said sharing linear portion integrates said adjacent wavy annular members with each other.

DETAILED DESCRIPTION OF THE PREFERRED EMBODIMENTS

The embodiments of the stent of the present invention will be described below with reference to FIGS. 1 through 4.

Figure 1:
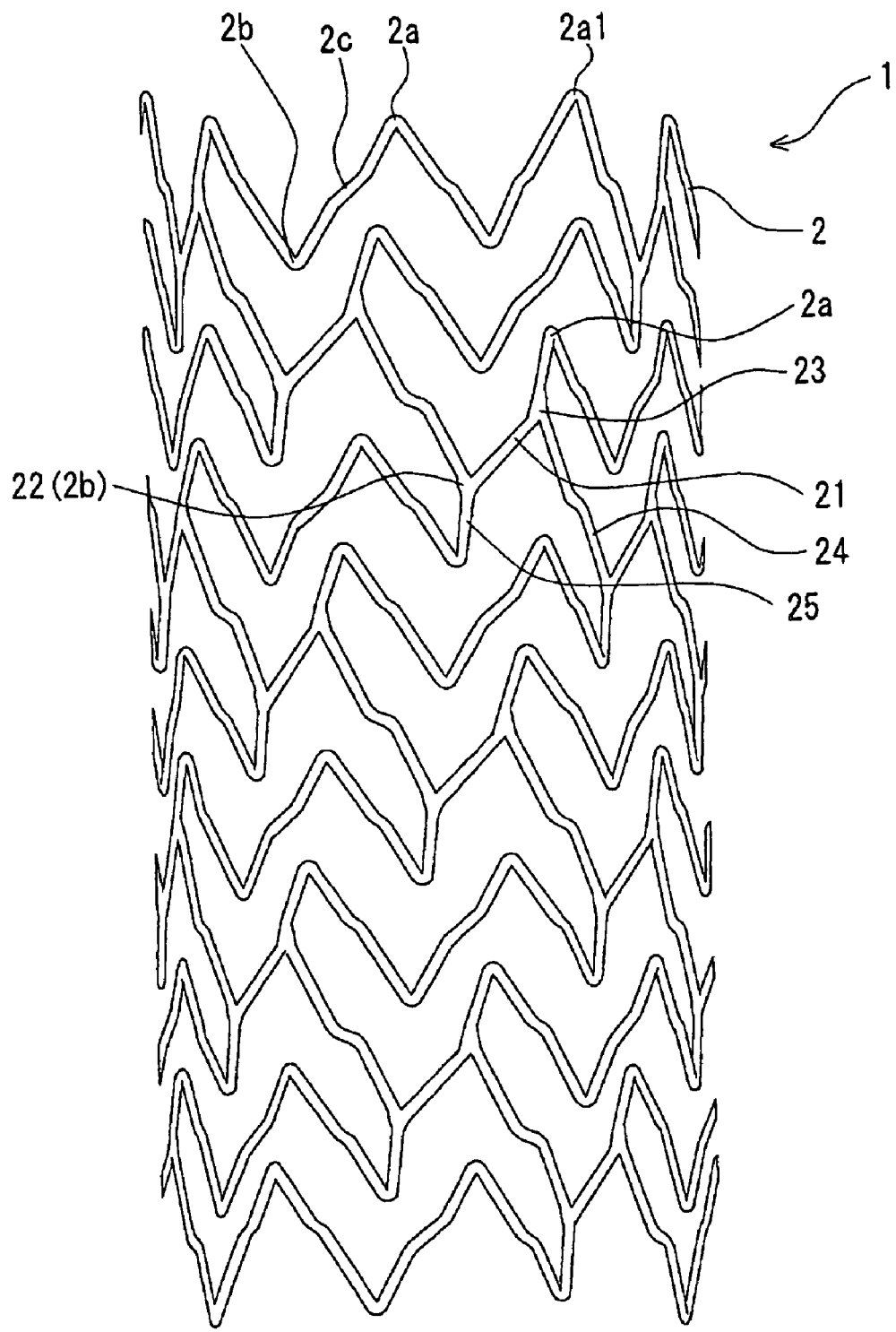
FIG. 1 is a front view showing a stent of one embodiment of the present invention.
Figure 2:
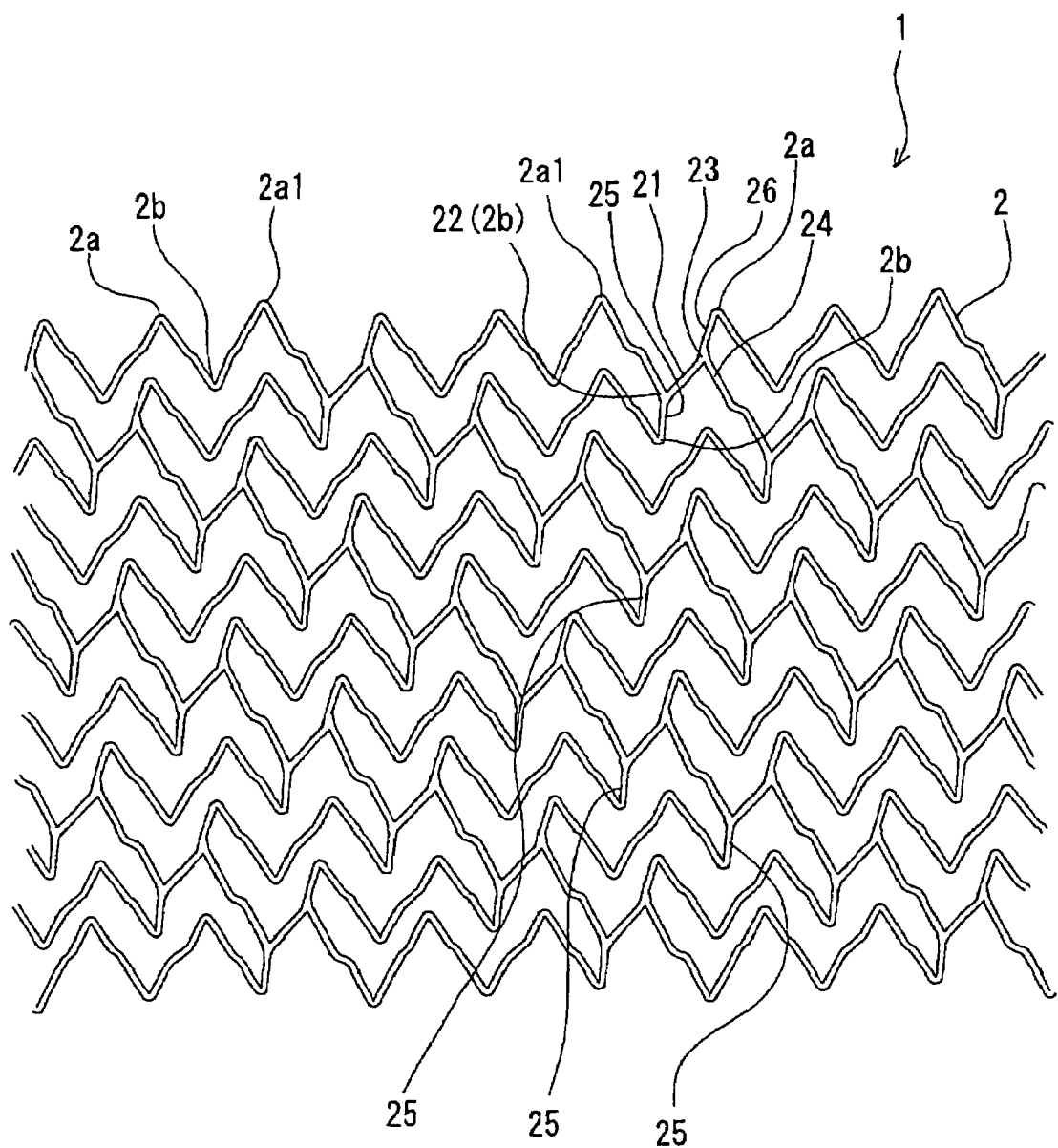
FIG. 2 is a development view showing the stent shown in FIG. 1.
Figure 3:
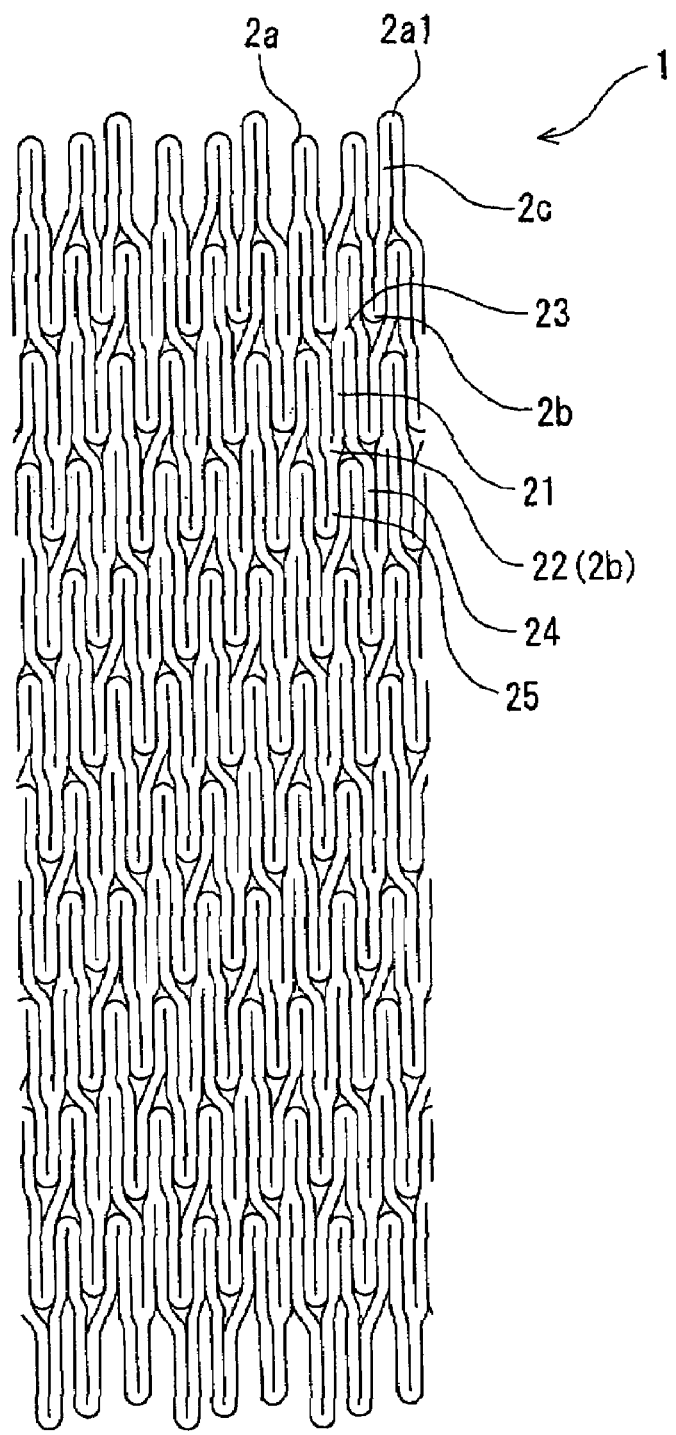
FIG. 3 is a development view showing the stent, shown in FIG. 1, when the stent is contracted.
Figure 4:
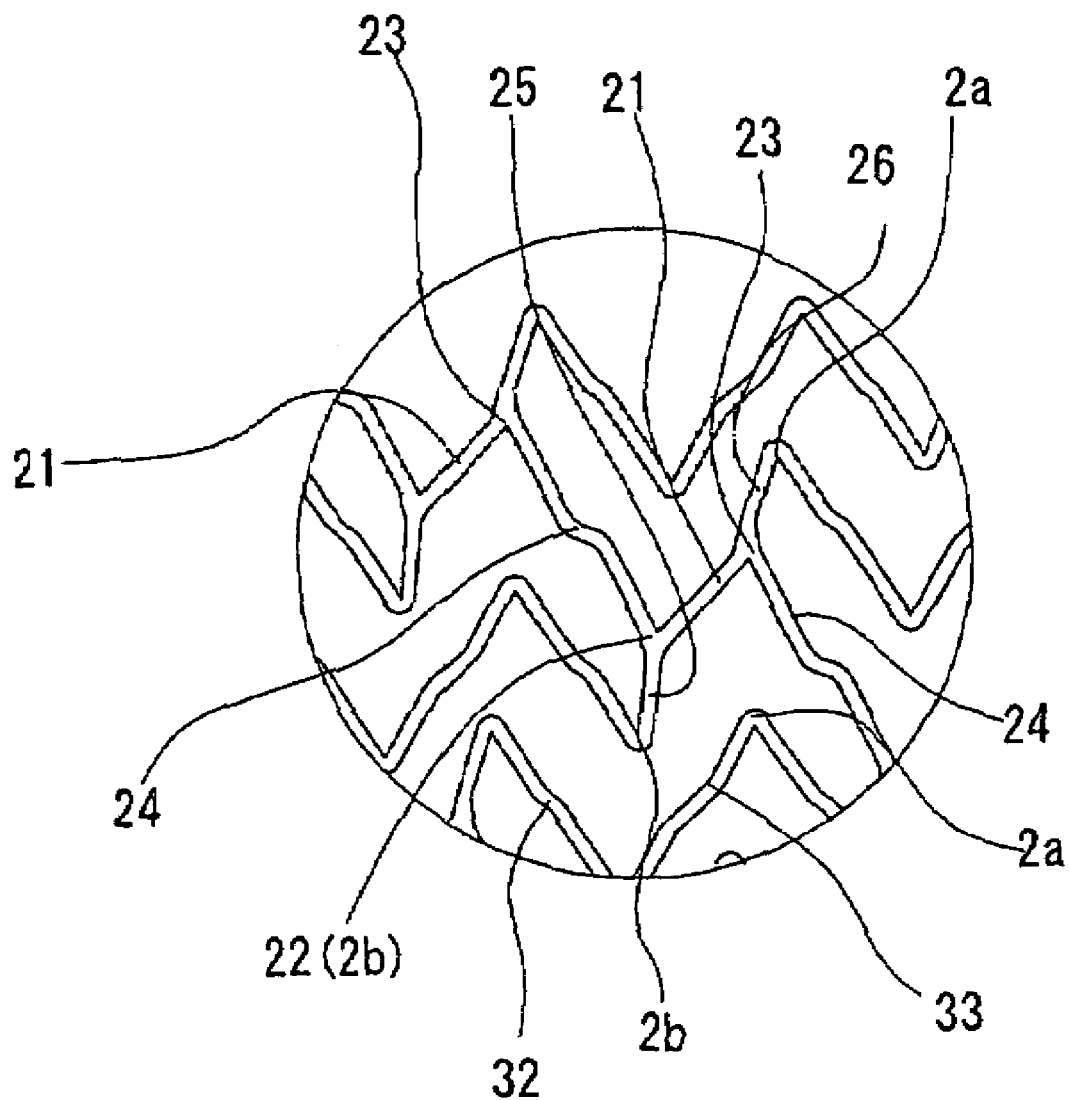
FIG. 4 is a partly enlarged view showing the stent shown in FIG. 1.

FIG. 1 is a front view showing a stent of an embodiment of the present invention. FIG. 2 is a development view showing the stent shown in FIG. 1. FIG. 3 is a development view showing the stent shown in FIG. 1, whose diameter is decreased. FIG. 4 is a partly enlarged view showing the stent shown in FIG. 1.

A stent 1 of the present invention to be implanted in an organism has a plurality of wavy annular members 2 arranged in an axial direction thereof. Each of the wavy annular members 2 has a plurality of one-end side bent portions each having an apex 2a at a one-end side of the stent 1 in the axial direction thereof and a plurality of other-end side bent portions each having an apex 2b at an other-end side of the stent 1 in the axial direction thereof. In the wavy annular members disposed adjacently to each other in the axial direction of the stent, the wavy annular member disposed at the one-end side of the stent in the axial direction thereof has a sharing linear portion 21 having a start point 22 at the apex 2b of one of the other-end side bent portions thereof or in the vicinity of the apex 2b and a termination point 23 between the apex 2b of the other-end side bent portion thereof and the apex 2a of one of the one-end side bent portions thereof. The sharing linear portion 21 integrates the adjacent wavy annular members with each other.

The stent of the present invention has the partial sharing portions which integrate adjacent wavy annular members with each other respectively. That is, the stent does not have a portion serving as only a connection portion of connecting the adjacent wavy annular members with each other, but is composed of portions each displaying an expansive force.

The stent 1 is the so-called self-expandable stent which is formed substantially cylindrically, decreased in its diameter when it is inserted into the organism, and is capable of returning to a configuration before its diameter is decreased, when it is implanted in the organism. FIG. 1 shows the outlook of the stent 1 when it is expanded.

The number of the wavy annular members 2 forming the stent 1 shown in FIG. 1 is set to 11. The number of the wavy annular members 2 is favorably in the range of 2 to 150 and more favorably in the range of 5 to 100, although the number thereof is different in dependence on the length of the stent.

Each of the wavy annular members 2 has a plurality of the one-end side bent portions each having the apex at one-end side of the stent 1 in the axial direction thereof and a plurality of the other-end side bent portions each having the apex at the other-end side of the stent 1 in the axial direction thereof. In addition, each of the wavy annular members 2 is composed of a large number of endless wavy line elements. The one-end side bent portions and the other-end side bent portions of each of the wavy annular members 2 are formed alternately. The number of the one-end side bent portions and that of the other-end side bent portions are equal to each other. The number of the one-end side bent portions (other-end side bent portions) of each of the wavy annular members 2 shown in FIG. 1 is set to nine. The number of the one-end side bent portions (other-end side bent portions) thereof is favorably in the range of 4 to 20 and more favorably in the range of 6 to 12. The wavy line element composing the wavy annular member 2 of the stent 1 of this embodiment curves and has a few straight portions. The wavy line element forming the annular member 2 has a sufficiently large length, thus display a high expansive force when the stent 1 expands. The axial length of the wavy annular member 2 is favorably in the range of 1 to 10 mm and more favorably in the range of 1.5 to 5 mm.

As shown in FIGS. 1, 2, 3, and 4, in the stent of this embodiment each of the wavy annular members 2 has a big wavy portion forming a projected one-end side apex $2a1$ projected closer to the one-end of the stent 1 than the apexes $2a$ of other one-end side bent portions and a projected other-end side apex (in this embodiment, coincident with start point) 22 projected closer to the other-end of the stent 1 than the apexes 2b of other other-end side bent portions. In this embodiment the wavy annular member 2 has a plurality of big wavy portions. In the stent 1, one wavy annular member 2 has nine one-end side bent portions and three big wavy portions. The three big wavy portions are substantially equiangularly formed with respect to the axis of the stent 1.

The one-end side wavy annular members 2 adjacent to the other-end side wavy annular member 2 in the axial direction of the stent 1 has a sharing linear portion 21 having the start point 22 at the apex 2b of one of the other-end side bent portions thereof or in the vicinity of the apex 2b and the termination point 23 between the apex 2b of the other-end side bent portion thereof and the apex 2a of one of the one-end side bent portions thereof. The sharing linear portion 21 integrates the adjacent wavy annular members with each other.

More specifically, the sharing linear portion 21 has its start point 22 at the apex 2b of one of the other-end side bent portions of the wavy annular members 2 disposed at the one-end side of the stent 1 in the axial direction thereof. The start point 22 is coincident with the apex 2b. The sharing linear portion 21 has its termination point 23 between the above-described apex 2b and the apex 2a of one of the one-end side bent portions thereof continuous with the apex 2b (coincident with start point 22). In this embodiment the sharing linear portion 21 has its termination point in the vicinity of approximately the midpoint between the apex 2b (coincident with start point 22) of the other end-side bent portion and the apex 2a of the one-end side bent portion continuous with the apex 2b. It is preferable to dispose the termination point 23 at the midpoint between the apexes 2b and 2a. But the termination point 23 may be shifted to the side of the apex 2a or to the side of the apex 2b with respect to the midpoint by $\frac{1}{100}$ to $\frac{49}{100}$ of the whole length between the apex 2b (or start point 22) and the apex 2a of the one-end side bent portion continuous with the apex 2b. But in this case, it is preferable that the termination point 23 is shifted to the side of the apex 2a with respect to the midpoint.

Because the stent 1 has the above-described construction, the stent 1 has a bifurcating portion (in other words, start point bifurcating portion) formed by a start point of the sharing linear portion 21 and a bifurcating portion (in other words, termination point bifurcating portion) formed by a termination point of the sharing linear portion 21. More specifically, the start point bifurcating portion bifurcates toward the one-end of the stent 1 from the start point 22 serving as a bifurcation point. The termination point bifurcating portion bifurcates toward the other-end of the stent 1 from the termination point 23 serving as a bifurcation point.

In the stent 1 of this embodiment, the linear portion disposed between the projected one-end side apex 2a1 of the big wavy portion and the projected other-end side apex (coincident with start point 22) thereof form a long linear portion longer than linear portions connecting adjacent apexes to each other respectively. As described above, the other end of the long linear portion is coincident with the sharing linear portion 21. In this embodiment, the sharing linear portion 21 is formed as a portion of the big wavy portion.

As shown in FIG. 2, in the stent 1 of this embodiment, each wavy annular member 2 has a short linear portion 26 connecting the termination point 23 of the sharing linear portion 21 thereof and the apex 2a of the one-end side bent portion thereof to each other. As shown in FIG. 2, the wavy annular member 2 integrated with the adjacent wavy annular member 2 having the short linear portion 26 by means of the sharing linear portion 21 has a short linear portion 25 connecting the start point 22 of the sharing linear portion 21 and the apex 2b of the other-end side bent portion thereof to each other and a long linear portion 24 connecting the termination point 23 of the sharing linear portion 21 and the other apex 2b of the other-end side bent portion thereof to each other. Thus the long linear portion 24 is composed of the linear portion between the projected one-end side apex (coincident with termination point 23) of the big wavy portion and the projected other-end side apex (coincident with start point 22 of sharing linear portions of wavy annular member adjacently disposed at other-end side of stent). That is, when the sharing linear portions 21 of the stent 1 adjacent to each other in the axial direction thereof are viewed from the one end of the axial direction thereof, the long linear portion 24 connects the termination point 23 of one sharing linear portion 21 and the start point 22 of the adjacent sharing linear portion 21 to each other. Therefore a zigzag composed of repetition of the unit of the long linear portion 24 and the sharing linear portion 21 form a spiral in a direction from the one end of the stent toward the other end thereof.

The stent 1 does not have any connection portions. Thus the stent does not have interruptions of curvature or deterioration in the expansive force caused by the formation of the connection portion. Thereby the stent displays a uniform expanded state retention force.

The stent 1 of this embodiment has a plurality of sharing linear portions 21 between the wavy annular members 2 adjacent to each other in the axial direction thereof. More specifically, three sharing linear portions 21 are formed between the adjacent wavy annular members 2. The three sharing linear portions 21 are substantially equiangularly formed with respect to the axis of the stent 1.

In the stent 1, the short linear portions 25 each connecting the start point 22 of the sharing linear portion 21 and the apex 2b of the other-end side bent portion to each other are formed not continuously in the axial direction of the stent 1, but a line connecting the short linear portions 25 to each other is substantially straight. As shown in FIG. 4, in the stent 1, each linear portion has a curved portion 32 in the vicinity of a middle position thereof (long linear portion and other linear portions) except the short linear portions 25, 26. The curved portion 32 makes the progress directions of linear portions almost parallel with each other and shifts the progress directions thereof to some extent in the axial direction of the stent. The curved portion 32 allows the linear portions to be long and the stent to have a high expansive force.

The length of the long linear portion 24 (length between termination point 23 of one sharing linear portion 21 and start point 22 of adjacent sharing linear portion 21) is a little larger than the length of the sum of the length of the sharing linear portion 21 and that of the short linear portion 25 (length between termination point 23 of one sharing linear portion 21 and apex 2b across start point 22). Thereby it is possible to prevent the apex 2b from excessively approaching a linear portion 33 (linear portion which connects the apex 2a and 2b to each other and does not form sharing linear portion nor has branch portion) of the adjacent wavy annular member and decrease the degree of nonuniformity of the axial length of a closed space (as shown in FIG. 2, in this embodiment, closed space is formed by letter V connected with letter M) formed by wavy annular members. Thereby the stent displays a high expanded state retention force.

As shown in FIG. 2, the apex 2a of each of the one-end side bent portions of each wavy annular member 2 penetrates into a space formed between the apexes 2b of the adjacent other-end side bent portions of one of the adjacent wavy annular members 2. The apex 2b of each of the other-end side bent portions of each wavy annular member 2 penetrates into a space formed between the apexes 2a of the adjacent one-end side bent portions 21 of the other of the adjacent wavy annular members 2. Thereby it is possible to form the long wavy annular member constituting the stent and decrease the area of the closed space (as shown in FIG. 2, in this embodiment closed space is formed by letter V connected with letter M) formed by the wavy annular member. Thereby the stent displays a high expanded state retention force.

When the stent 1 of this embodiment contracts, as shown in FIG. 3, wavy line elements are arranged, with gaps very little present in the circumferential direction of the stent 1. Therefore the stent 1 has a high coverage.

Figure 5:
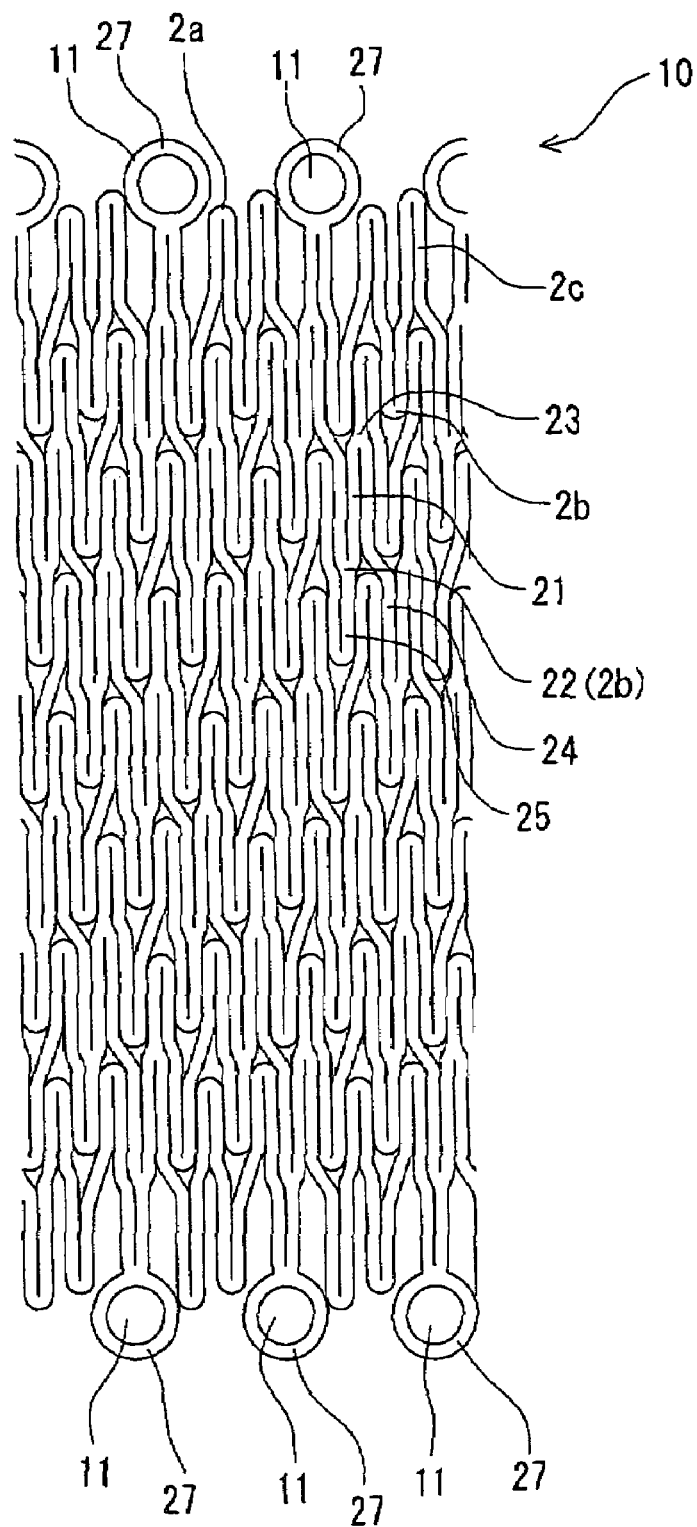
FIG. 5 is a development view showing another embodiment of the stent of the present invention, when the stent is contracted.

It is preferable to provide the stent 10 shown in FIG. 5 with a marker 11. It is favorable to dispose the marker 11 at an end of the stent 10. It is more favorable to dispose the marker 11 at both ends of the stent. More specifically, as shown in FIG. 5, it is preferable to dispose a plurality of the markers 11 at both ends of the stent.

The stent 10 of this embodiment has an opening 27 formed at an apex disposed at one end of the stent. The marker 11 is fixed to the stent to close the opening 27.

It is preferable to mount the marker 11 on a small opening formed on the stent by pressing a disk-shaped member disposed on a small opening. The disk-shaped member is made of an X-ray contrast material having a portion a little smaller than the small opening and a portion a little larger than the small opening. Thereafter the disk-shaped member is pressed in a direction from both surfaces thereof to caulk it to the small opening like a rivet.

It is possible to use an X-ray contrast marker, an ultrasonic wave contrast marker, and the like. The marker is made of contrast substances such as an X-ray contrast substance, an ultrasonic wave contrast substance, and the like. As materials of the marker, it is preferable to use gold, platinum, tungsten, tantalum, iridium, palladium, alloys of these metals, a gold-palladium alloy, a platinum-iridium alloy, NiTiPd, and NiTiAu.

Figure 6:
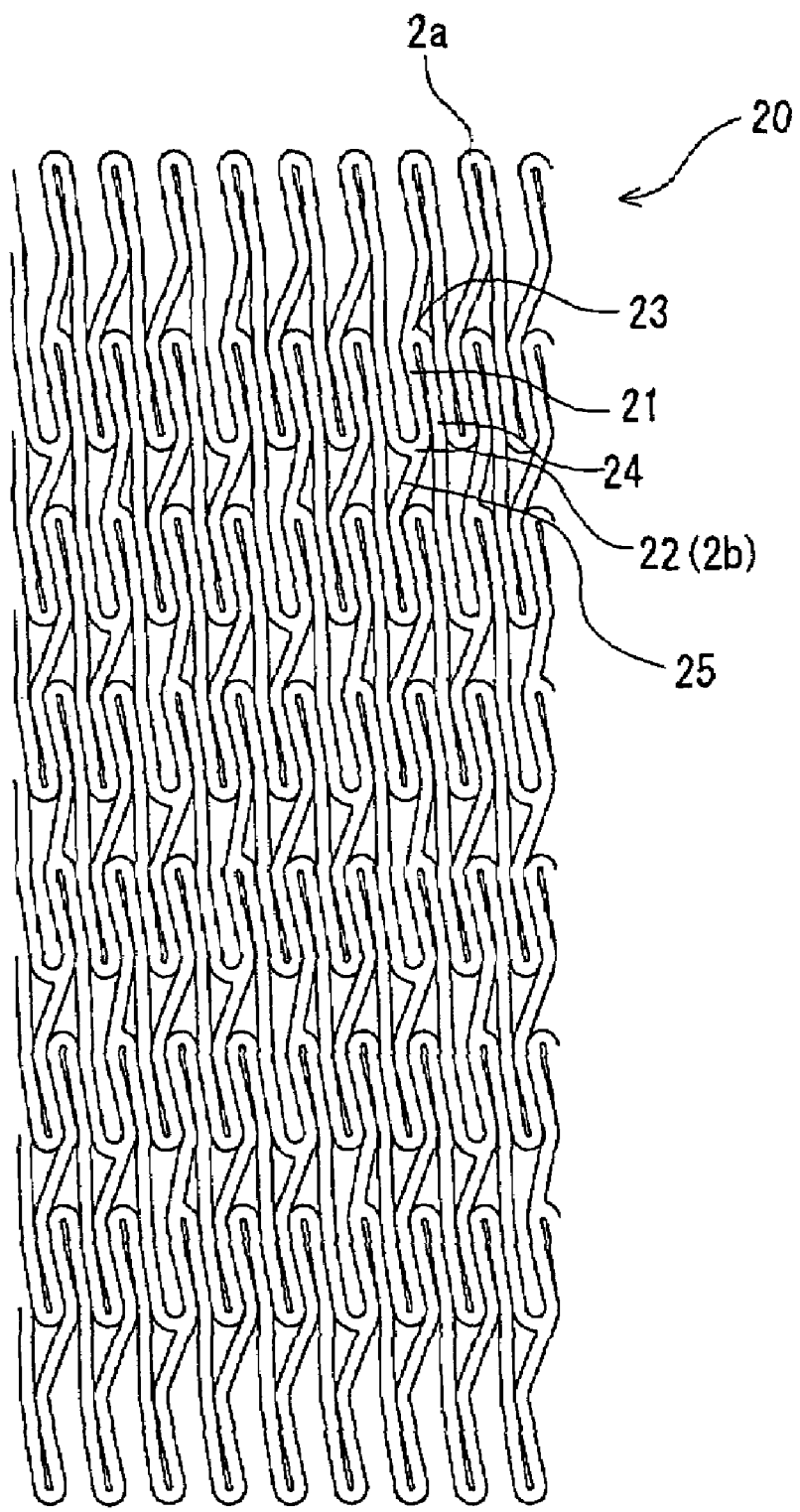
FIG. 6 is a development view showing still another embodiment of the stent of the present invention, when the stent is contracted.

The stent of the present invention may be formed as a stent 20 having a construction as shown in FIG. 6. FIG. 6 is a development view showing still another embodiment of the stent of the present invention.

The stent 20 has the same construction as that of the stent 1 except that the big wavy portion is not formed in each wavy annular member 2 thereof and that each wave has approximately the same size. Another difference is that in the stent 20, a gap is formed beside a portion forming the sharing linear portion 21.

Figure 7:
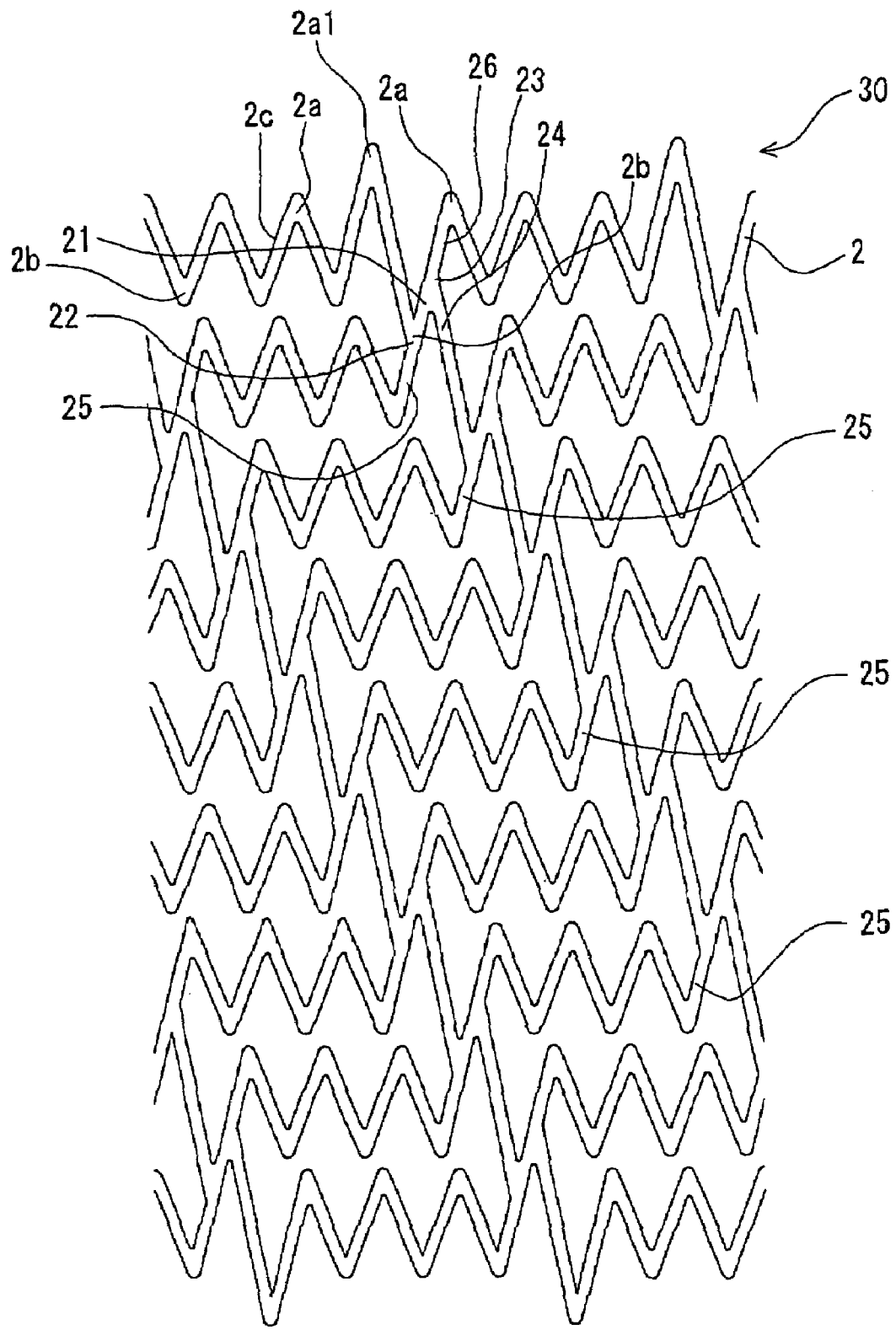
FIG. 7 is an explanatory view for explaining a pattern of still another embodiment of the stent of the present invention.

The stent of the present invention may be formed as a stent 30 having a construction as shown in FIG. 7. FIG. 7 is an explanatory view for explaining a pattern of still another embodiment of the stent of the present invention.

The stent 30 has the same construction as that of the stent 1 except the number of the one-end side bent portions of one wavy annular member 2, that of the other-end side bent portions thereof, and that of the sharing linear portions 21 integrating the adjacent wavy annular members with each other. The number of the one-end side bent portions and the other-end side bent portions of one wavy annular member 2 of the stent 30 is smaller than that of one wavy annular member 2 of the stent 1. More specifically, the number of the one-end side bent portions and the other-end side bent portions of one wavy annular member 2 of the stent 30 are eight respectively. One wavy annular member 2 has two big wavy portions opposed to each other with respect to the axis of the stent 30. The adjacent two wavy annular members are integrated with each other by two sharing linear portions 21. The two sharing linear portions 21 are opposed to each other with respect to the axis of the stent 30.

Figure 8:
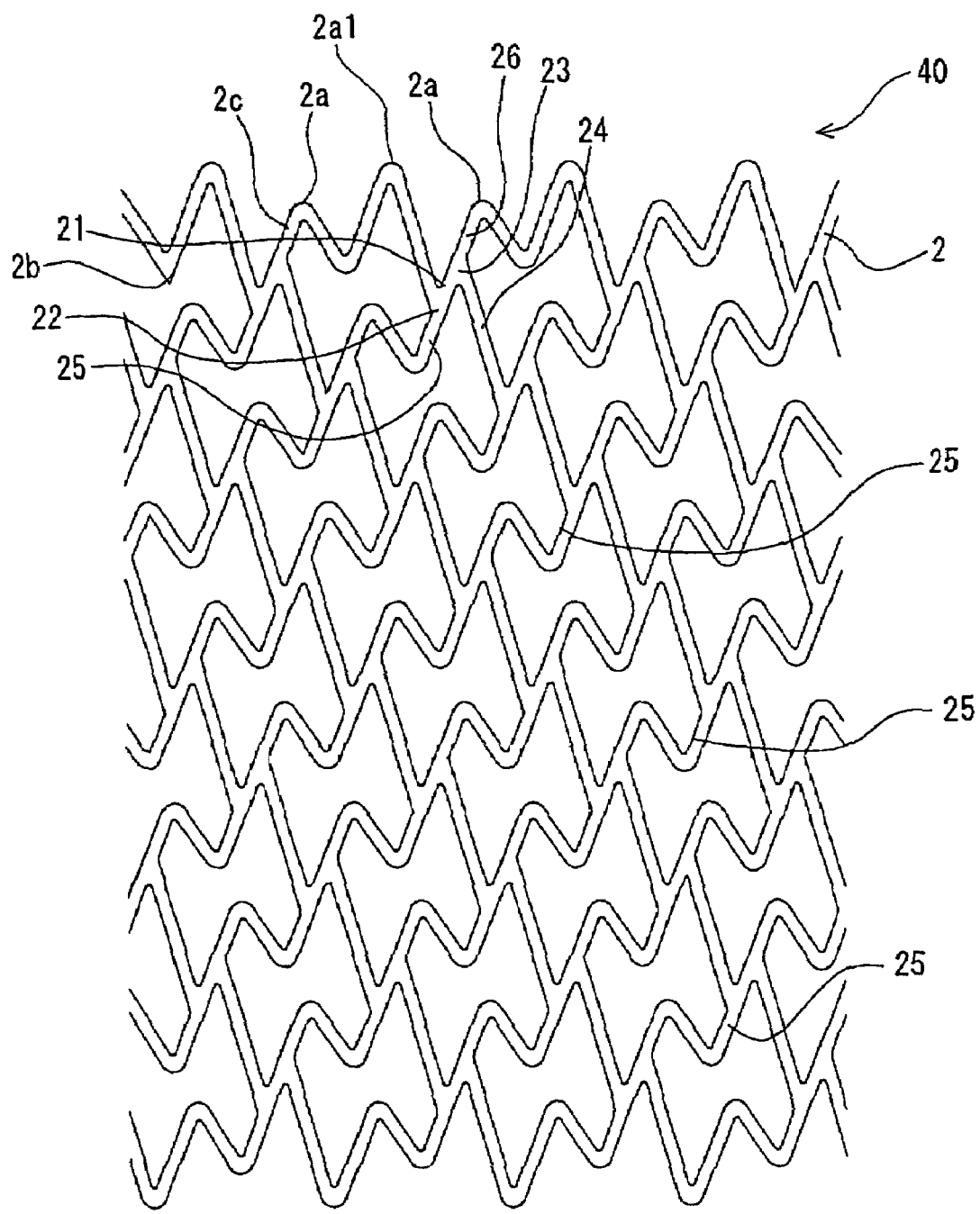
FIG. 8 is an explanatory view for explaining a pattern of still another embodiment of the stent of the present invention.

The stent of the present invention may be formed as a stent 40 having a construction as shown in FIG. 8. FIG. 8 is an explanatory view for explaining a pattern of still another embodiment of the stent of the present invention.

The stent 40 has the same construction as that of the stent 1 except the number of the one-end side bent portions of one wavy annular member 2, that of the other-end side bent portions thereof, and that of the sharing linear portions 21 integrating the adjacent wavy annular members with each other. In the stent 40, the number of the one-end side bent portions and the other-end side bent portions of one wavy annular member 2 of the stent 40 is smaller than that of one wavy annular member 2 of the stent 1. More specifically, the number of the one-end side bent portions and the other-end side bent portions of one wavy annular member 2 of the stent 40 are eight respectively. One wavy annular member 2 has four big wavy portions substantially equiangularly formed with respect to the axis of the stent 40. The adjacent two wavy annular members are integrated with each other by four sharing linear portions 21. The four sharing linear portions 21 are substantially equiangularly formed with respect to the axis of the stent 40.

The diameter of each of the stent of the above-described embodiment decreases when a load is applied radially inward from the entire peripheral surface thereof.

Figure 9:
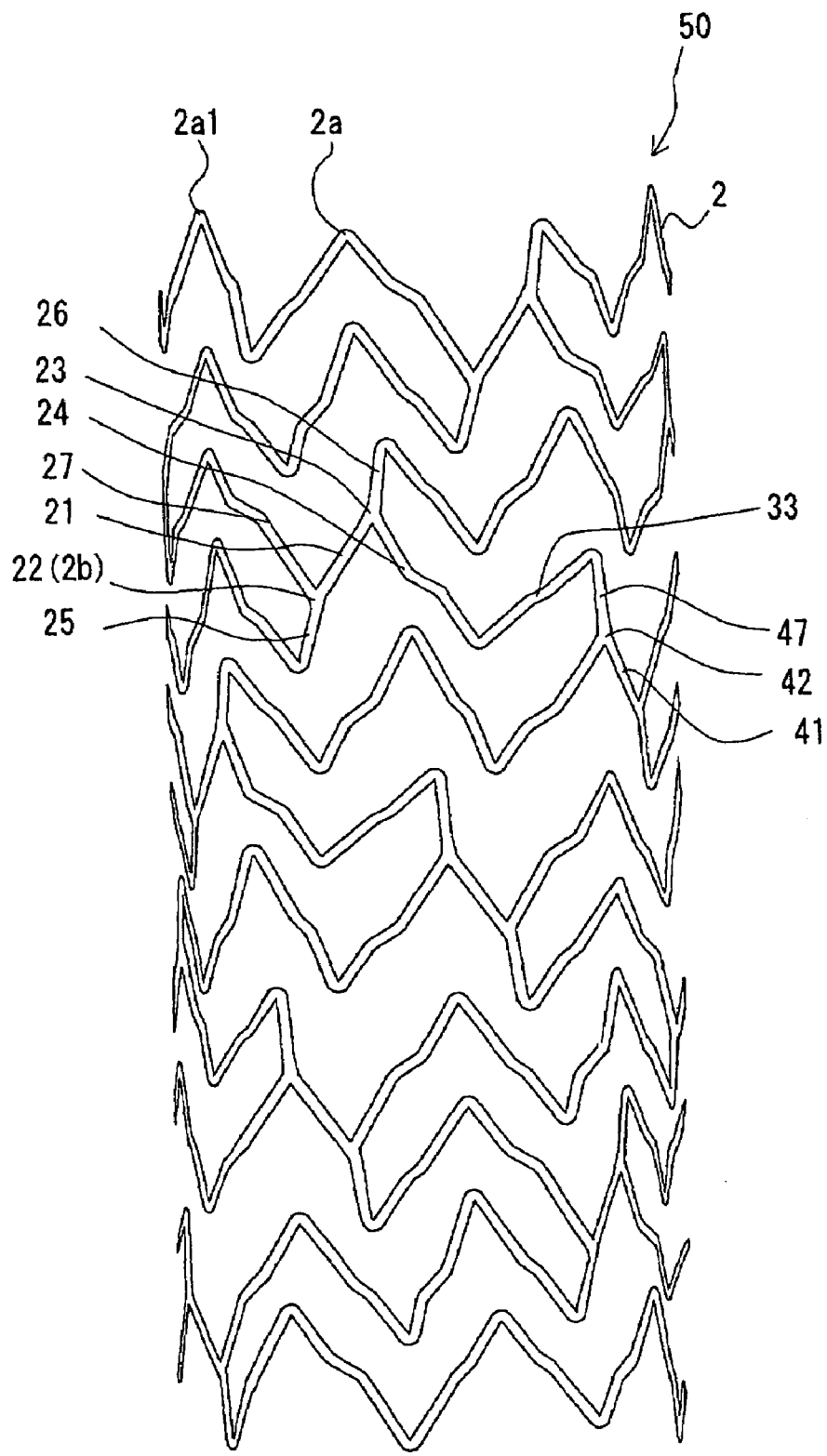
FIG. 9 is a front view showing still another embodiment of the stent of the present invention.
Figure 10:
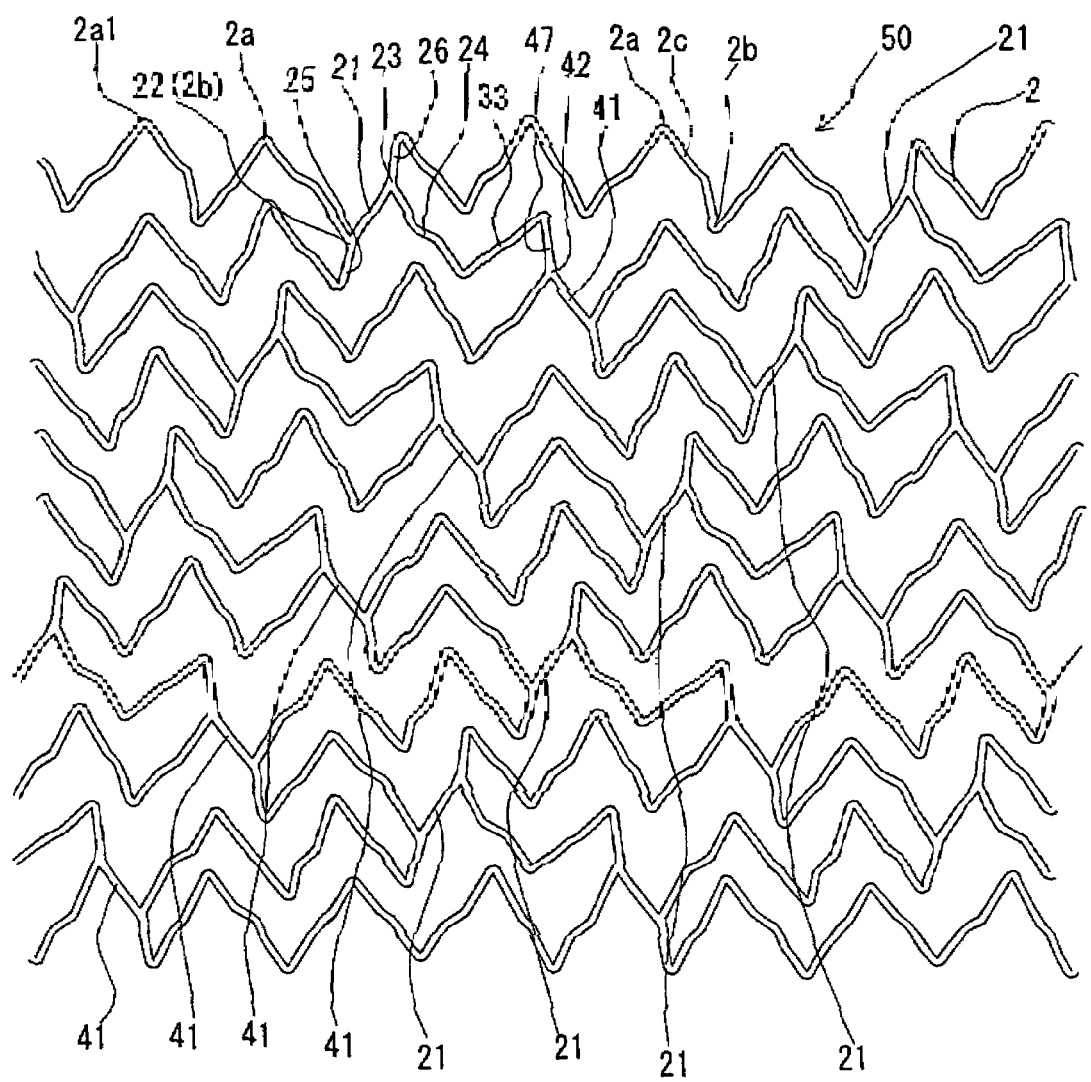
FIG. 10 is a development view showing the stent shown in FIG. 9.
Figure 11:
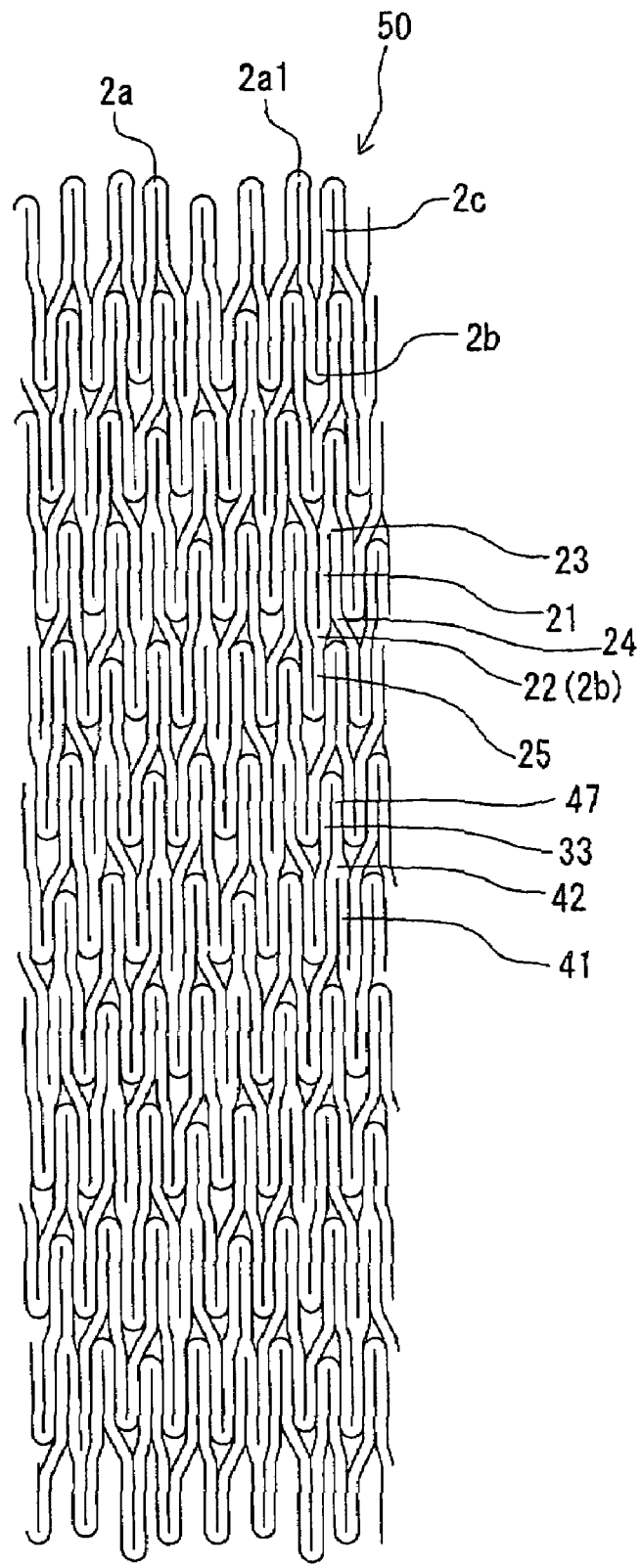
FIG. 11 is a development view showing the stent, shown in FIG. 9, when the stent is contracted.

The stent of the present invention may be formed as a stent 50 having a construction as shown in FIGS. 9 through 11. FIG. 9 is a front view showing still another embodiment of the stent of the present invention. FIG. 10 is a development view showing the stent shown in FIG. 9. FIG. 11 is a development view showing the stent, shown in FIG. 9, whose diameter is decreased.

The stent 50 has the same construction as that of the stent 1 except the number of the one-end side bent portions of one wavy annular member 2, the number of the other-end side bent portions, the number of the sharing linear portions 21 integrating the adjacent wavy annular members with each other, the arrangement form of the sharing linear portions, and the orientation thereof.

The number of the one-end side bent portions of one wavy annular member 2 of the stent 50 and that of the other-end side bent portions thereof are smaller than that of one wavy annular member 2 of the stent 1. More specifically, the number of the one-end side bent portions of one wavy annular member 2 of the stent 50 and that of the other-end side bent portions of one wavy annular member 2 thereof are eight respectively. Eleven wavy annular members 2 are disposed in the axial direction of the stent 50. The adjacent two wavy annular members 2 are integrated with each other by two sharing linear portions 21 (first pattern sharing linear portion 21) or two sharing linear portions 41 (second pattern sharing linear portion 41). The two sharing linear portions 21 are opposed to each other with respect to the axis of the stent 50. Similarly the two sharing linear portions 4 are opposed to each other with respect to the axis of the stent 50.

In the stent 50, the first pattern sharing linear portion 21 and the second pattern sharing linear portion 41 are disposed alternately with respect to the axial direction thereof. Further, the first pattern sharing linear portion 21 and the second pattern sharing linear portion 41 are disposed uncontinuously with each other in the axial direction of the stent 50. More specifically, the second pattern sharing linear portion 41 is shifted from the first pattern sharing linear portion 21 in the circumferential direction of the stent 50.

In the stent 50, the first pattern sharing linear portion 21 and the second pattern sharing linear portion 41 extend obliquely with respect to the axial direction of the stent and are different from each other in the orientation thereof.

More specifically, in the stent 50, one annular member 2 has two big wavy portions formed at positions opposed to each other with respect to the axis thereof. The adjacent two wavy annular members 2 are integrated with each other by two sharing linear portions. In the stent 50, the termination point of the first pattern sharing linear portion 21 of one wavy annular member 2 is connected to the other-end side bent portion thereof by a linear portion 24. Similarly the termination point of the second pattern sharing linear portion 41 of one wavy annular member 2 is connected to the other-end side bent portion thereof by the linear portion 24. That is, in the stent 1, the long linear portion 24 connects two sharing linear portions (exactly, termination point of sharing linear portion of one wavy annular member and start point of sharing linear portion of adjacent wavy annular member are connected to each other) adjacent to each other in the axial direction of the stent 1 to each other. On the other hand, in the stent 50, the linear portion 24 does not connect the sharing linear portions to each other. The linear portion 24 connected with the sharing linear portion is not formed as dearly as the long linear portion 24 of the stent 1. The linear portion 24 of the stent 50 is a little longer than other linear portions but may be formed as a long linear portion.

In the stent 50, one one-end side bent portion and one other-end side bent portion are disposed between the first pattern sharing linear portion 21 and the second pattern sharing linear portion 41 adjacent to the first pattern sharing linear portion 21 in the axial direction thereof. Two first pattern sharing linear portions 21 adjacent to each other in the axial direction of the stent are substantially equiangularly disposed with respect to the axis of the stent 50. Similarly two second pattern sharing linear portions 41 adjacent to each other in the axial direction thereof are also substantially equiangularly disposed with respect to the axis thereof. Thereby the stent 50 is capable of entirely displaying a substantially uniform expansive force.

As shown in FIG. 10, in the stent 50, the first pattern sharing linear portions 21 are spirally disposed in the axial direction thereof. Similarly the second pattern sharing linear portions 41 are spirally disposed in the axial direction thereof.

As shown in FIG. 10, the stent 50 has 11 wavy annular members arranged in the axial direction thereof. The first pattern sharing linear portions 21 are spirally disposed in the axial direction thereof. Similarly the second pattern sharing linear portions 41 are spirally disposed in the axial direction thereof. More specifically, the adjacent wavy annular members are connected with each other by two first pattern sharing linear portions 21. The first pattern sharing linear portions 21 are spirally disposed in the axial direction of the stent 50 to form two spirals. Each of the two spirals is composed of five first pattern sharing linear portions 21. Similarly the adjacent wavy annular members (not connected by first pattern sharing linear portion 21) are connected with each other by two second pattern sharing linear portions 41. The second pattern sharing linear portions 41 are spirally disposed in the axial direction of the stent 50 to form two spirals. Each of the two spirals is constructed of five second pattern sharing linear portions 41.

As described above, the first pattern sharing linear portions 21 and the second pattern sharing linear portions 41 extend obliquely with respect to the axial direction of the stent 50 and are different from each other in the orientation thereof. It is preferable that the orientation of the first pattern sharing linear portion 21 and that of the second pattern sharing linear portion 41 are substantially symmetrical to each other with respect to the axis of the stent. Thereby the stent 50 is capable of entirely displaying a substantially uniform expansive force.

As shown in FIG. 10, one wavy annular member 2 of the stent 50 has a short linear portion 26 connecting the termination point 23 of the first pattern sharing linear portion 21 thereof and the apex 2a of the one-end side bent portion thereof to each other. The wavy annular member adjacent to the wavy annular member 2 having the short linear portion 26 has a short linear portion 25 connecting the start point 22 of the first pattern sharing linear portion 21 thereof and the apex 2b of the other-end side bent portion thereof to each other and a short linear portion 47 connecting a termination point 42 of the second pattern sharing linear portion 41 thereof and the apex of the one-end side bent portion thereof to each other.

The construction of the stent 50 of this embodiment is different from that of the stent 1. The construction of the stent 50 makes a resistance to an axial expansion and contraction of the wavy annular member smaller than the resistance thereto in the stent 1. Thereby the stent 50 has more favorable follow-up performance for deformation of blood vessels.

Figure 12:
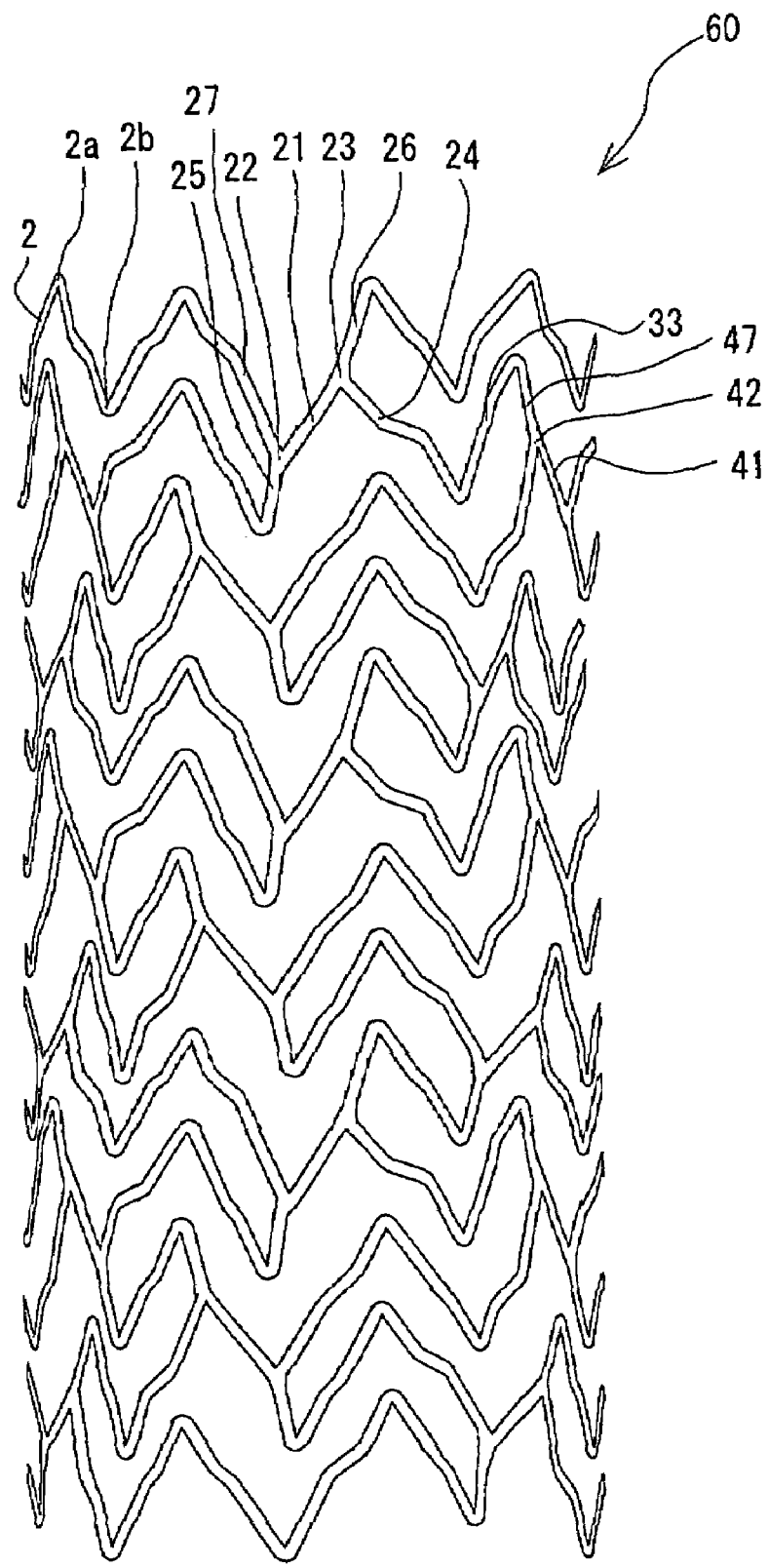
FIG. 12 is a front view showing still another embodiment of the stent of the present invention.
Figure 13:
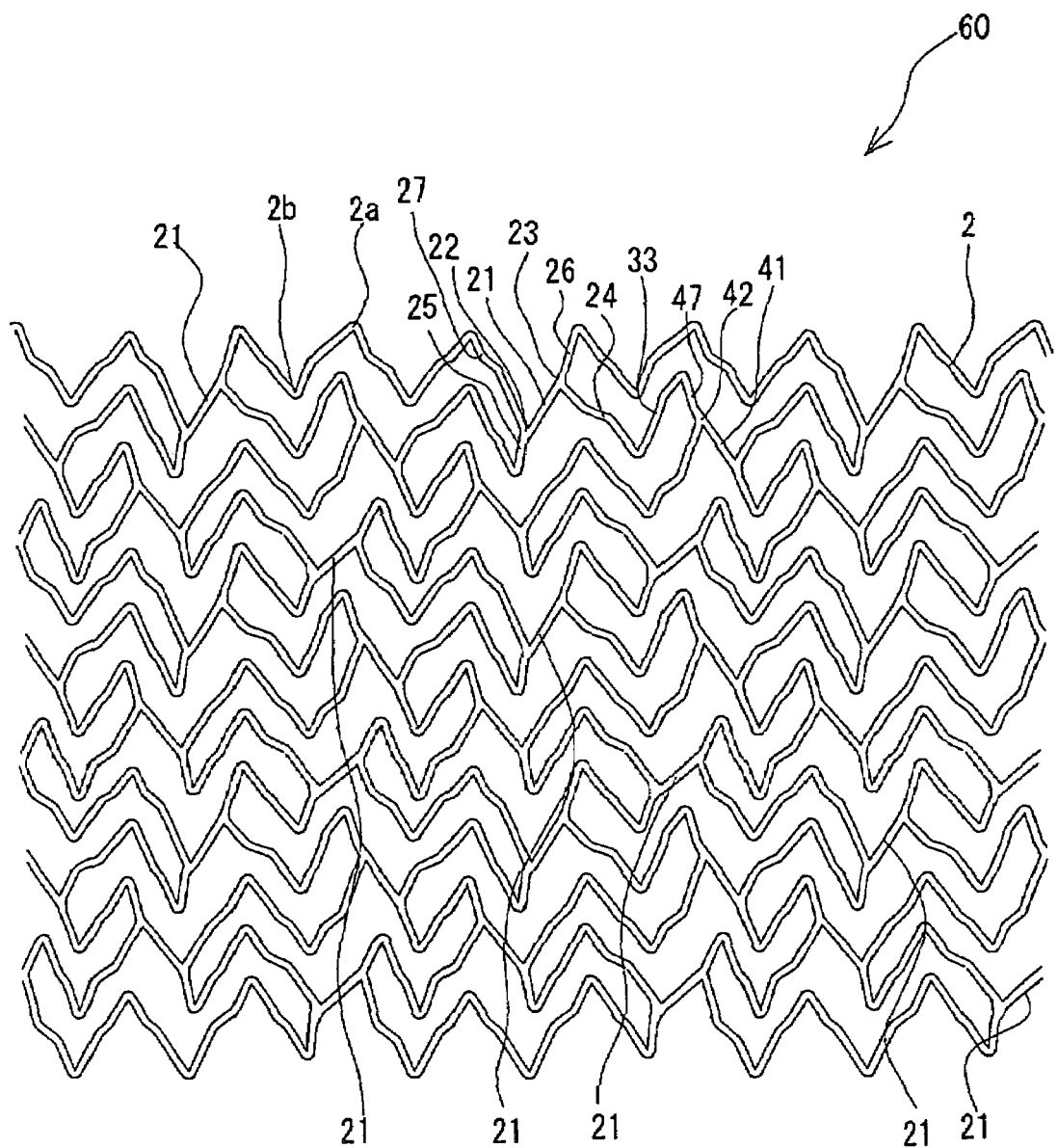
FIG. 13 is a development view showing the stent shown in FIG. 12.
Figure 14:
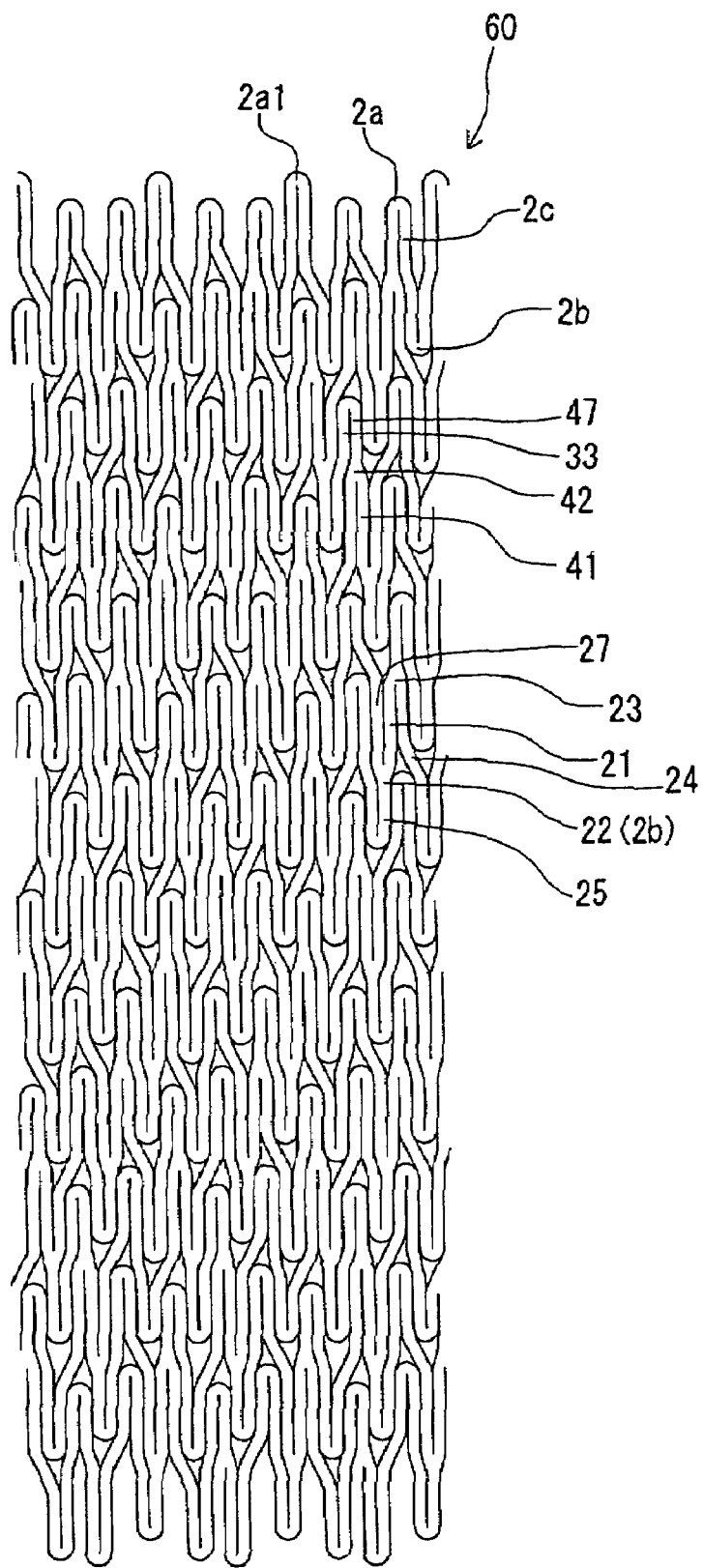
FIG. 14 is a development view showing the stent shown in FIG. 12, when the stent is contracted.

The stent of the present invention may be formed as a stent 60 having a construction as shown in FIGS. 12 through 14. FIG. 12 is a front view showing still another embodiment of the stent of the present invention. FIG. 13 is a development view showing the stent shown in FIG. 12. FIG. 14 is a development view showing the stent, shown in FIG. 12, whose diameter is decreased.

The stent 60 has the same construction as that of the stent 1 except the arrangement form of the sharing linear portion and the orientation thereof. In the stent 60, the sharing linear portions (first pattern sharing linear portion) 21 and the sharing linear portions (second pattern sharing linear portion) 41 are formed substantially straight respectively in the axial direction of the stent 60.

In the stent 60, the number of the one-end side bent portions of one wavy annular member 2 thereof and that of the other-end side bent portions thereof are equal to that of the wavy annular member 2 of the stent 1. More specifically, the number of the one-end side bent portions of the wavy annular member 2 and that of the other-end side bent portions are nine respectively. Thirteen wavy annular members 2 are arranged in the axial direction of the stent 60. The adjacent two wavy annular members 2 are integrated with each other by three sharing linear portions 21 (first pattern sharing linear portion 21) or by three sharing linear portions 41 (second pattern sharing linear portion 41). The three sharing linear portions 21 are substantially equiangularly disposed in the axial direction of the stent 60. Similarly the three sharing linear portions 41 are substantially equiangularly disposed in the axial direction of the stent 60.

The sharing linear portions (first pattern sharing linear portion) 21 and the sharing linear portions (second pattern sharing linear portion 41) extend obliquely with respect to the axial direction of the stent 60 and are different from each other in the orientation thereof.

More specifically, in the stent 60, the termination point of the first pattern sharing linear portion 21 of one wavy annular member 2 is connected to the other-end side bent portion thereof by the linear portion 24. Similarly the termination point of the second pattern sharing linear portion 41 of one wavy annular member 2 is connected to the other-end side bent portion thereof by the linear portion 24. That is, in the stent 1, the linear portion 24 connects two sharing linear portions (exactly, termination point of sharing linear portion of one wavy annular member and start point of sharing linear portion of adjacent wavy annular member are connected to each other) adjacent to each other in the axial direction of the stent 1. On the other hand, in the stent 60, the linear portion 24 does not connect the sharing linear portions to each other. The linear portion 24 connected with the sharing linear portion is not formed as clearly as the long linear portion 24 of the stent 1. The linear portion 24 of the stent 60 is a little longer than other linear portions but may be formed as a long linear portion.

In the stent 60, one one-end side bent portion and one other-end side bent portion are disposed between the first pattern sharing linear portion 21 and the second pattern sharing linear portion 41 adjacent to the first pattern sharing linear portion 21 in the axial direction thereof. Two first pattern sharing linear portions 21 adjacent to each other in the axial direction of the stent are substantially equiangularly disposed with respect to the axis of the stent 60. Similarly two second pattern sharing linear portions 41 adjacent to each other in the axial direction of the stent are also substantially equiangularly disposed with respect to the axis of the stent 60. Therefore the stent 60 is capable of entirely displaying a substantially uniform expansive force.

As shown in FIG. 13, the stent 60 has 13 wavy annular members arranged in the axial direction thereof. The first pattern sharing linear portions 21 are spirally disposed in the axial direction thereof. Similarly the second pattern sharing linear portions 41 are spirally disposed in the axial direction thereof. More specifically, the adjacent wavy annular members are connected with each other by three first pattern sharing linear portions 21 or three second pattern sharing linear portions 41 alternating with the three first pattern sharing linear portions 21 in the axial direction of the stent 60. The first pattern sharing linear portion 21 are spirally disposed in the axial direction of the stent 60 to form three spirals. Each of the three spirals is composed of six first pattern sharing linear portions 21. Similarly the second pattern sharing linear portions 41 are spirally disposed in the axial direction of the stent 60 to form three spirals. Each of the three spirals is composed of six second pattern sharing linear portions 41.

As described above, the first pattern sharing linear portions 21 and the second pattern sharing linear portions 41 extend obliquely with respect to the axial direction of the stent 60 and are different from each other in the orientation thereof. It is preferable that the orientation of the first pattern sharing linear portion 21 and that of the second pattern sharing linear portion 41 are substantially symmetrical to each other with respect to the axis of the stent 60. Thereby the stent 60 is capable of entirely displaying a substantially uniform expansive force.

Describing the arrangement manner of the sharing linear portions in the axial direction of the stent 60, three first pattern sharing linear portions 21 are formed at uniform intervals in the circumferential direction of the stent. Three second pattern sharing linear portions 41 are formed adjacently to the first pattern sharing linear portions 21 at uniform intervals in the circumferential direction of the stent. Three second pattern sharing linear portions 41 are formed adjacently to the above-described second pattern sharing linear portions 41 at uniform intervals in the circumferential direction of the stent.

Three first pattern sharing linear portions 21 are formed adjacently to the above-described second pattern sharing linear portions 41 at uniform intervals in the circumferential direction of the stent. In this manner, the first pattern sharing linear portion 21 and the second pattern sharing linear portion 41 are arranged in the order of 21, 41, 41, 21, 21, 41, 41 . . . .

The construction of the stent 60 makes a resistance to an axial expansion and contraction of the wavy annular member smaller than the resistance thereto in the stent 1. Thereby the stent 60 has more favorable follow-up performance for deformation of blood vessels.

Figure 15:
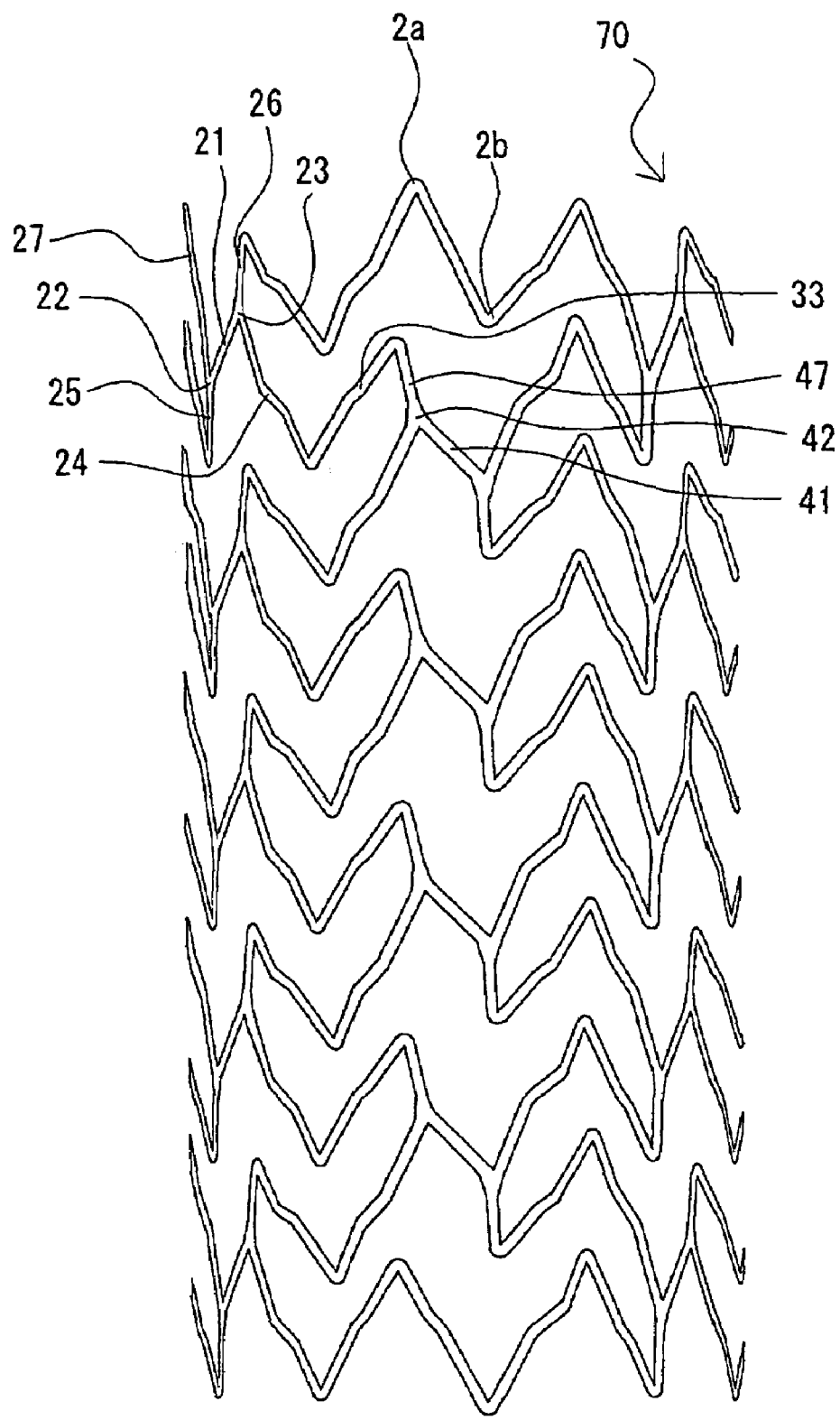
FIG. 15 is a front view showing still another embodiment of the stent of the present invention.
Figure 16:
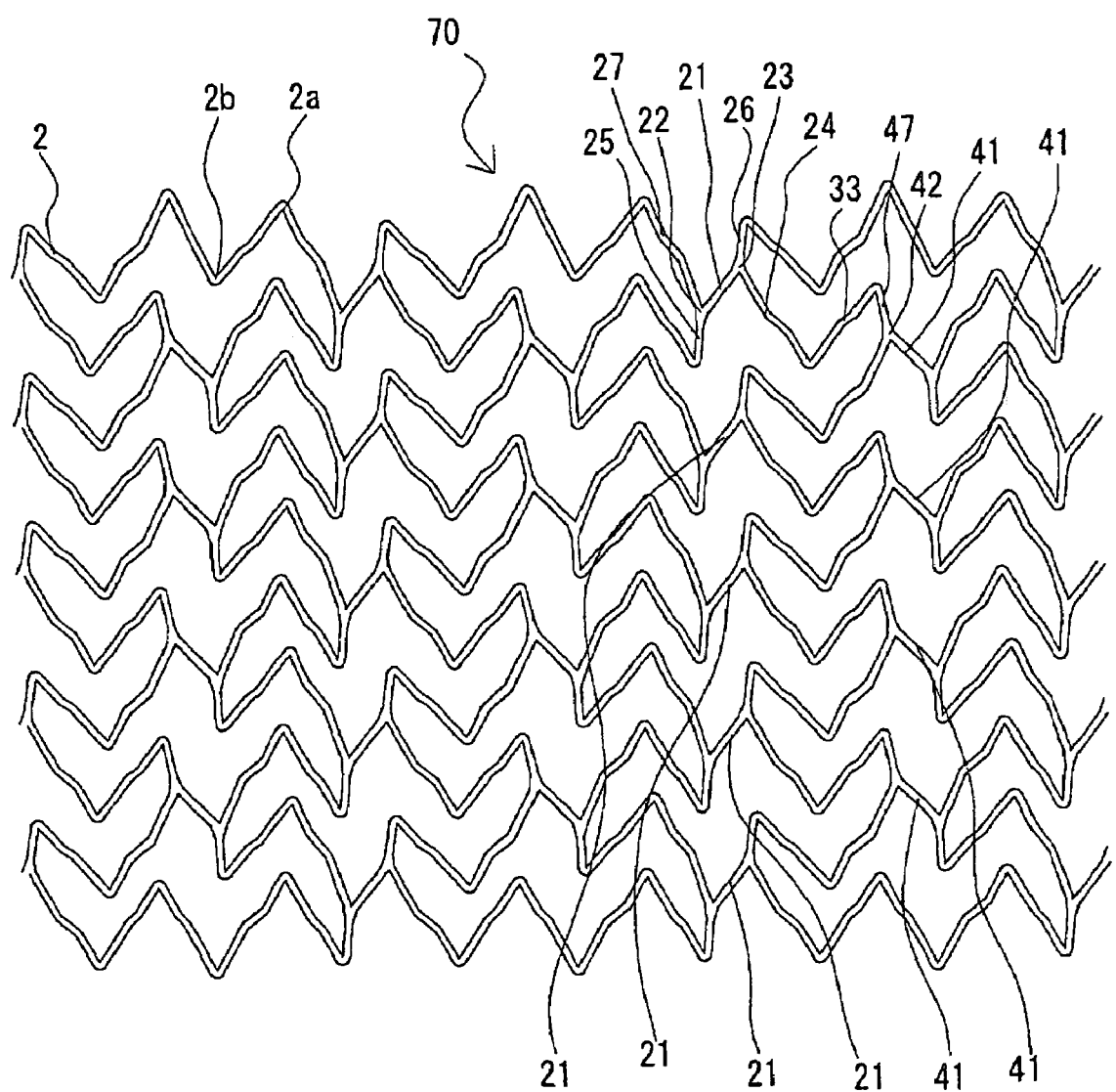
FIG. 16 is a development view showing the stent shown in FIG. 15.
Figure 17:
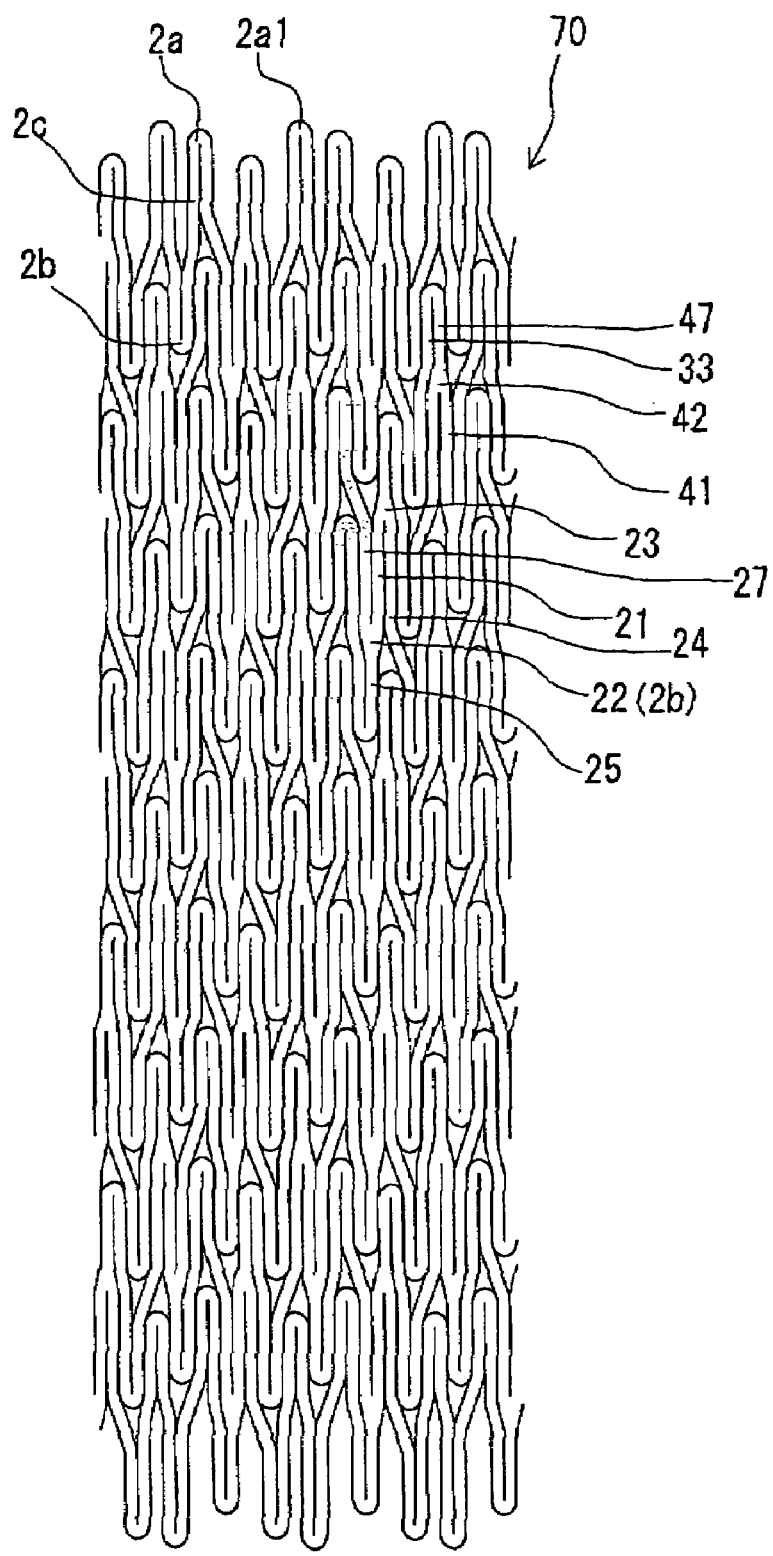
FIG. 17 is a development view showing the stent, shown in FIG. 15, when the stent is contracted.

The stent of the present invention may be formed as a stent 70 having a construction as shown in FIGS. 15 through 17. FIG. 15 is a front view showing still another embodiment of the stent of the present invention. FIG. 16 is a development view showing the stent shown in FIG. 15. FIG. 17 is a development view showing the stent, shown in FIG. 15, whose diameter is decreased.

The stent 70 has the same construction as that of the stent 1 except the arrangement form of the sharing linear portion and the orientation thereof.

In the stent 70, the number of the one-end side bent portions of one wavy annular member 2 and that of the other-end side bent portions thereof are equal to than that of the wavy annular member 2 of the stent 1. More specifically, the number of the one-end side bent portions of the wavy annular member 2 and that of the other-end side bent portions thereof are nine respectively. Ten wavy annular members 2 are disposed in the axial direction of the stent 70. The adjacent two wavy annular members 2 are integrated with each other by three sharing linear portions 21 (first pattern sharing linear portion 21) or three sharing linear portions 41 (second pattern sharing linear portion 41). The three sharing linear portions 21 are substantially equiangularly disposed in the axial direction of the stent 70. Similarly the three sharing linear portions 41 are substantially equiangularly disposed in the axial direction thereof.

In the stent 70, the sharing linear portions (first pattern sharing linear portion) 21 and the sharing linear portions (second pattern sharing linear portion) 41 are disposed alternately in the axial direction of the stent 70. Further, the first pattern sharing linear portions (first pattern sharing linear portion) 21 and the sharing linear portions (second pattern sharing linear portion) 41 are disposed uncontinuously with each other in the axial direction of the stent 70. More specifically, the sharing linear portion (second pattern sharing linear portion) 41 is shifted from the sharing linear portion (first pattern sharing linear portion) 21 in the circumferential direction of the stent 70. The sharing linear portions (first pattern sharing linear portion) 21 are formed substantially straight in the axial direction of the stent 70. Similarly the sharing linear portions (second pattern sharing linear portion) 41 are formed substantially straight in the axial direction of the stent 70.

In the stent 70, the first pattern sharing linear portion 21 and the second pattern sharing linear portion 41 extend obliquely with respect to the axial direction of the stent and are different from each other in the orientation thereof.

More specifically, in the stent 70, the termination point of the first pattern sharing linear portion 21 of one wavy annular member 2 is connected to the other-end side bent portion thereof by the linear portion 24. Similarly the termination point of the second pattern sharing linear portion 41 of one wavy annular member 2 is connected to the other-end side bent portion thereof by the linear portion 24. That is, in the stent 1, the long linear portion 24 connects two sharing linear portions (exactly, termination point of sharing linear portion of one wavy annular member and start point of sharing linear portion of adjacent wavy annular member are connected to each other) adjacent to each other in the axial direction of the stent 1. On the other hand, in the stent 70, the linear portion 24 does not connect the sharing linear portions to each other. The linear portion 24 connected with the sharing linear portion is not formed as clearly as the long linear portion 24 of the stent 1. The linear portion 24 of the stent 70 is a little longer than other linear portions but may be formed as a long linear portion.

In the stent 70, one one-end side bent portion and one other-end side bent portion are disposed between the first pattern sharing linear portion 21 and the second pattern sharing linear portion 41 adjacent to the first pattern sharing linear portion 21 in the axial direction thereof. Two first pattern sharing linear portions 21 adjacent to each other in the axial direction of the stent are substantially equiangularly disposed with respect to the axis of the stent 70. Similarly two second pattern sharing linear portions 41 adjacent to each other in the axial direction of the stent are also substantially equiangularly disposed with respect to the axis of the stent 70. Therefore the stent 70 is capable of entirely displaying a substantially uniform expansive force.

As described above, the first pattern sharing linear portions 21 and the second pattern sharing linear portions 41 extend obliquely with respect to the axial direction of the stent 70 and are different from each other in the orientation thereof. It is preferable that the orientation of the first pattern sharing linear portion 21 and that of the second pattern sharing linear portion 41 are substantially symmetrical to each other with respect to the axis of the stent. Thereby the stent 70 is capable of entirely displaying a substantially uniform expansive force. Describing the arrangement manner of the sharing linear portions in the axial direction of the stent, three first pattern sharing linear portions 21 are formed at uniform intervals in the circumferential direction of the stent. Three second pattern sharing linear portions 41 are formed adjacently to the first pattern sharing linear portions 21 at uniform intervals in the circumferential direction of the stent. Three first pattern sharing linear portions 21 are formed adjacently to the above-described second pattern sharing linear portions 41 at uniform intervals in the circumferential direction of the stent.

Three second pattern sharing linear portions 41 are formed adjacently to the above-described first pattern sharing linear portions 21 at uniform intervals in the circumferential direction of the stent. In this manner, the first pattern sharing linear portion 21 and the second pattern sharing linear portion 41 are arranged in the order of 21, 41, 21, 41, 21, 41, 21 . . . .

The construction of the stent 70 makes a resistance to an axial expansion and contraction of the wavy annular member smaller than the resistance thereto in the stent 1. Thereby the stent 70 has more favorable follow-up performance for deformation of blood vessels.

73-2 As shown in FIG. 16, the wavy annular member 2 of the stent 70 has a short linear portion 26 connecting the termination point 23 of the first pattern sharing linear portion 21 thereof and the apex 2a of the one-end side bent portion thereof to each other. As shown in FIG. 15, the wavy annular member adjacent to the wavy annular member 2 having the short linear portion 26 has a short linear portion 25 connecting the start point 22 of the first pattern sharing linear portion 21 thereof and the apex 2b of the other-end side bent portion thereof to each other and a short linear portion 47 connecting a termination point 42 of the second pattern sharing linear portion 41 thereof and the apex of the one-end side bent portion thereof to each other.

Figure 18:
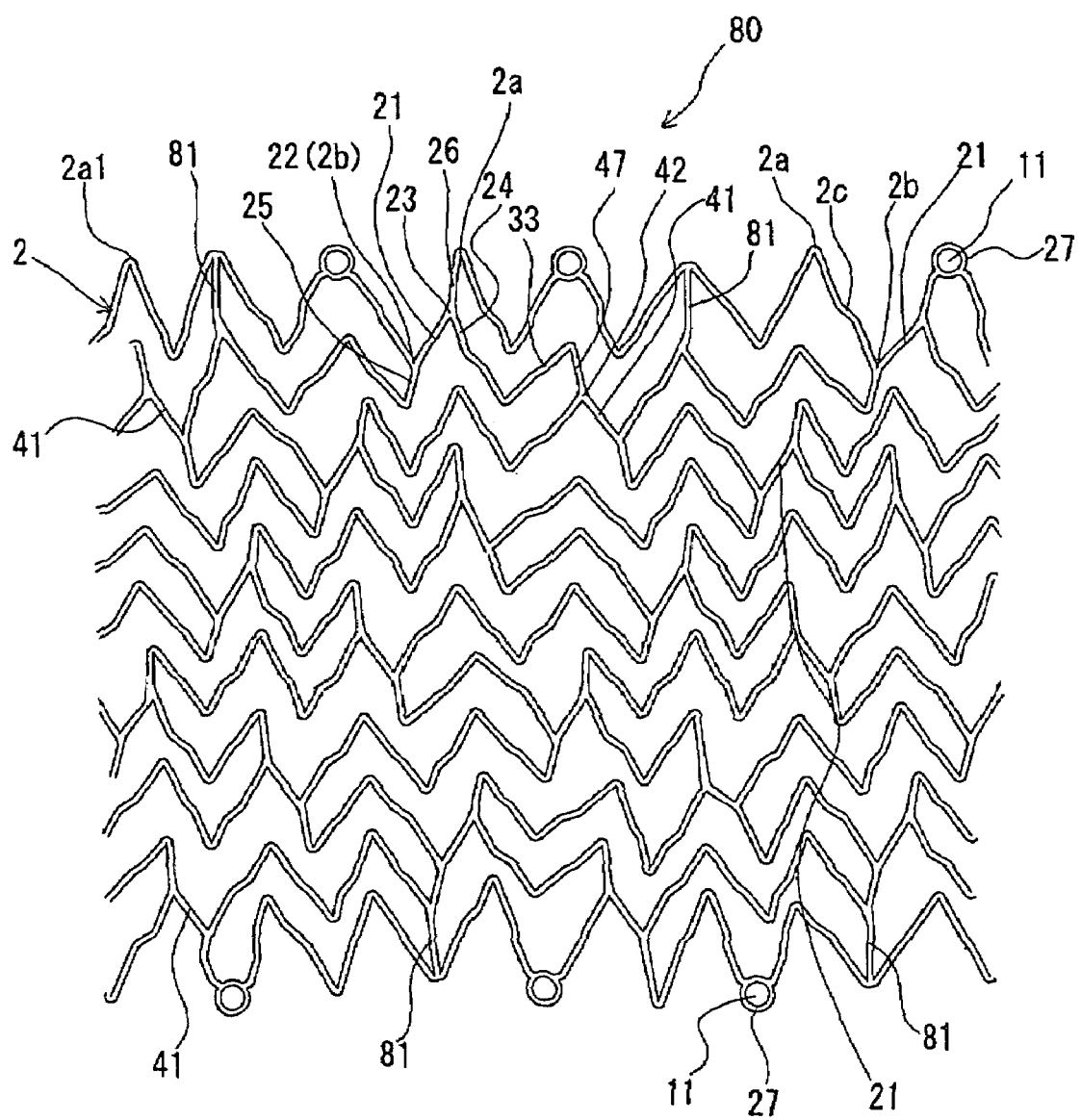
FIG. 18 is a development view showing still another embodiment of the stent of the present invention.
Figure 19:
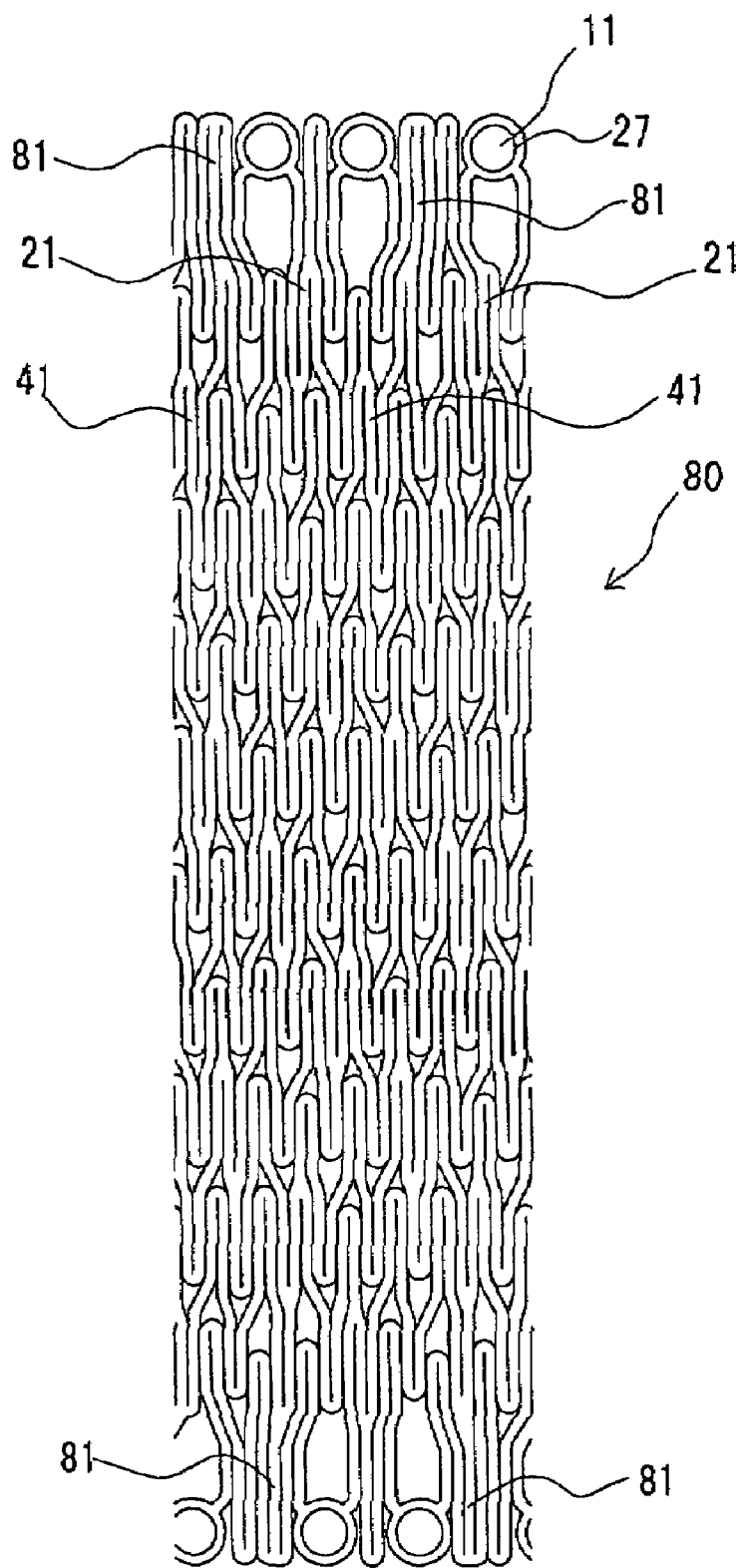
FIG. 19 is a development view showing the stent, shown in FIG. 18, when the stent is contracted.

The stent of the present invention may be formed as a stent 80 having a construction as shown in FIGS. 18 and 19. FIG. 18 is a front view showing still another embodiment of the stent of the present invention. FIG. 19 is a development view showing the stent shown in FIG. 18, when the stent contracted.

The stent 80 has the same construction as that of the stent 1 except the number of the one-end side bent portions of one wavy annular member, the number of the other-end side bent portions thereof, the number of the sharing linear portions integrating the adjacent wavy annular members with each other, the arrangement form of the sharing linear portions, the orientation thereof, the marker disposed at both ends of the stent and a coupling portion formed on the wavy annular member disposed at both ends of the stent.

The basic construction of the stent 80 is the same as that of the above-described stent 50.

The number of the one-end side bent portions of one wavy annular member 2 of the stent 50 and that of the other-end side bent portions thereof are smaller than that of one wavy annular member 2 of the stent 1. More specifically, the number of the one-end side bent portions of one wavy annular member 2 of the stent 80 and that of the other-end side bent portions of one wavy annular member 2 thereof are eight respectively. Eleven wavy annular members 2 are disposed in the axial direction of the stent 80. The adjacent two wavy annular members 2 are integrated with each other by two sharing linear portions 41 (first pattern sharing linear portion 21) or two sharing linear portions 41 (second pattern sharing linear portion 41). The two sharing linear portions 21 are opposed to each other with respect to the axis of the stent 80. Similarly the two sharing linear portions 41 are opposed to each other with respect to the axis of the stent 80.

In the stent 80, the first pattern sharing linear portion 21 and the second pattern sharing linear portion 41 are disposed alternately with respect to the axial direction thereof. Further, the first pattern sharing linear portion 21 and the second pattern sharing linear portion 41 are disposed uncontinuously with each other in the axial direction of the stent 80. More specifically, the second pattern sharing linear portion 41 is shifted from the first pattern sharing linear portion 21 in the circumferential direction of the stent 80.

In the stent 80, the first pattern sharing linear portion 21 and the second pattern sharing linear portion 41 extend obliquely with respect to the axial direction of the stent and are different from each other in the orientation thereof.

In the stent 80, one one-end side bent portion and one other-end side bent portion are disposed between the first pattern sharing linear portion 21 and the second pattern sharing linear portion 41 adjacent to the first pattern sharing linear portion 21 in the axial direction thereof. Two first pattern sharing linear portions 21 adjacent to each other in the axial direction of the stent and the two second pattern sharing linear portions 41 adjacent to each other in the axial direction thereof are substantially equiangularly disposed with respect to the axis thereof. Thereby the stent 80 is capable of entirely displaying a substantially uniform expansive force.

As shown in FIG. 18, in the stent 80, the first pattern sharing linear portions 21 are spirally disposed in the axial direction thereof. Similarly the second pattern sharing linear portions 41 are spirally disposed in the axial direction thereof.

As shown in FIG. 18, the stent 80 has 11 wavy annular members arranged in the axial direction thereof. The first pattern sharing linear portions 21 are spirally disposed in the axial direction thereof. Similarly the second pattern sharing linear portions 41 are spirally disposed in the axial direction thereof. More specifically, the adjacent wavy annular members are connected with each other by two first pattern sharing linear portions 21. The first pattern sharing linear portions 21 are spirally disposed in the axial direction of the stent 80 to form two spirals. Each of the two spirals is composed of five first pattern sharing linear portions 21. Similarly the adjacent wavy annular members (not connected by first pattern sharing linear portion 21) are connected with each other by two second pattern sharing linear portions 41. The second pattern sharing linear portions 41 are spirally disposed in the axial direction of the stent 80 to form two spirals. Each of the two spirals is constructed of five second pattern sharing linear portions 41.

As described above, the first pattern sharing linear portions 21 and the second pattern sharing linear portions 41 extend obliquely with respect to the axial direction of the stent 80 and are different from each other in the orientation thereof. It is preferable that the orientation of the first pattern sharing linear portion 21 and that of the second pattern sharing linear portion 41 are substantially symmetrical to each other with respect to the axis of the stent. Thereby the stent 80 is capable of entirely displaying a substantially uniform expansive force.

As shown in FIG. 18, one wavy annular member 2 of the stent 80 has a short linear portion 26 connecting the termination point 23 of the first pattern sharing linear portion 21 thereof and the apex 2a of the one-end side bent portion thereof to each other. The wavy annular member adjacent to the wavy annular member 2 having the short linear portion 26 has a short linear portion 25 connecting the start point 22 of the first pattern sharing linear portion 21 thereof and the apex 2b of the other-end side bent portion thereof to each other and a short linear portion 47 connecting a termination point 42 of the second pattern sharing linear portion 41 thereof and the apex of the one-end side bent portion thereof to each other.

Similarly to the stent shown in FIGS. 18 and 19, the stent 80 has a contrast marker 11. It is favorable to dispose the contrast marker 11 at an end of the stent 80. It is more favorable to dispose the contrast marker 11 at both ends of the stent. More specifically, as shown in FIGS. 18 and 19, it is preferable to dispose a plurality of the markers 11 at both ends of the stent. The stent 80 of this embodiment has an opening 27 formed at an apex disposed at both ends thereof. The marker 11 closing the opening 27 is fixed to the ends of the stent. The contrast marker is the same as that of the above-described stent 10.

As shown in FIGS. 18 and 19, an outer edge of the opening 27 is coincident with outer edges of other apexes disposed at the end (upper and lower ends) of the stent in the axial direction thereof. That is, in the stent 80, the outer edge of the opening 27 to which the marker is fixed is not projected outward from the outer edges of the other apexes disposed at the end of the stent. By making the outer edges of the stent coincident with one another in the axial direction of the stent, the stent can be securely pressed out even though the stent is curved. In the stent 80, the opening 27 is formed at an apex disposed at one end of the stent. The opening 27 has two leg portions extending toward other end of the stent. The two leg portions are spaced from each other and substantially parallel. In the stent 80, two leg portions are extended inward from a position located inward from an inner side of each opening 27 disposed at a bent portion, with the two leg portions spaced from each other at a predetermined interval. The two leg portions extended from the opening 27 are spaced from each other. That is, in the stent 80, the two leg portions extended from the opening 27 are not proximate to each other, unlike the leg portion of the stent 10 shown in FIG. 5. By spacing the two leg portions from each other at the predetermined interval, the configuration of the region in the vicinity of the marker-formed portion (opening 27) is stable. Therefore even though a strong force is applied to the region in the vicinity of the marker-formed portion (opening 27), the stent is prevented from deforming and can be reliably pressed out.

As shown in FIGS. 18 and 19, in the stent 80, the wavy annular member 2 disposed at both ends (upper and lower ends) of the stent is provided with a coupling portion 81 for coupling the wavy annular member 2 and the adjacent wavy annular member 2 to each other. In the stent 80, two coupling portions 81 are provided between the wavy annular member 2 disposed at both ends (upper and lower ends) of the stent and the adjacent wavy annular member 2. In the stent 80, coupling portion 81 is provided only between two wavy annular members 2 disposed at both ends (upper and lower ends) of the stent and the adjacent wavy annular member 2. The two coupling portions 81 are formed at positions opposed to each other with respect to the axis of the stent. As shown in FIGS. 18 and 19, at one end portion (upper end portion) of the stent 80, the two sharing linear portions 21 and the above-described two coupling portions 81 are disposed substantially equiangularly with respect to the axis of the stent. Similarly at the other end portion (lower end portion) of the stent 80, the two sharing linear portions 41 and the above-described two coupling portions 81 are disposed substantially equiangularly with respect to the axis of the stent.

Because the stent 80 has the sharing linear portions and the coupling portions at both end portions thereof, the form or the configuration of both end portions of the stent is stable after the stent expands. The above-described stent has two coupling portions at both end portions thereof. But the stent may have one or three coupling portions at both end portions thereof.

Because the stent 80 of this embodiment has a construction different from that of the stent 1, it has a comparatively low resistance to axial expansion and contraction thereof. Thereby the stent 80 has favorable follow-up performance for deformation of blood vessels.

Figure 20:
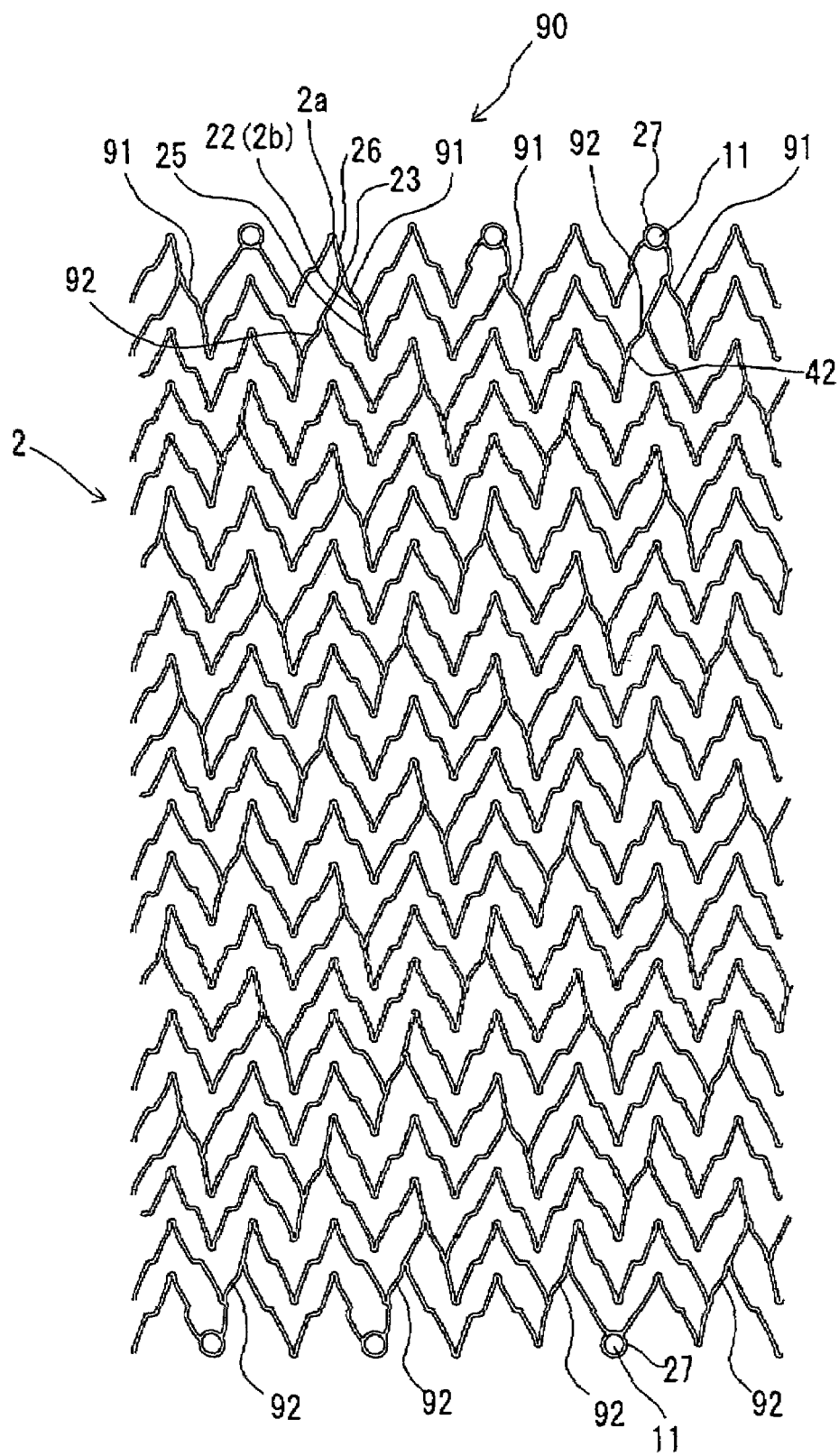
FIG. 20 is a development view showing still another embodiment of the stent of the present invention.
Figure 21:
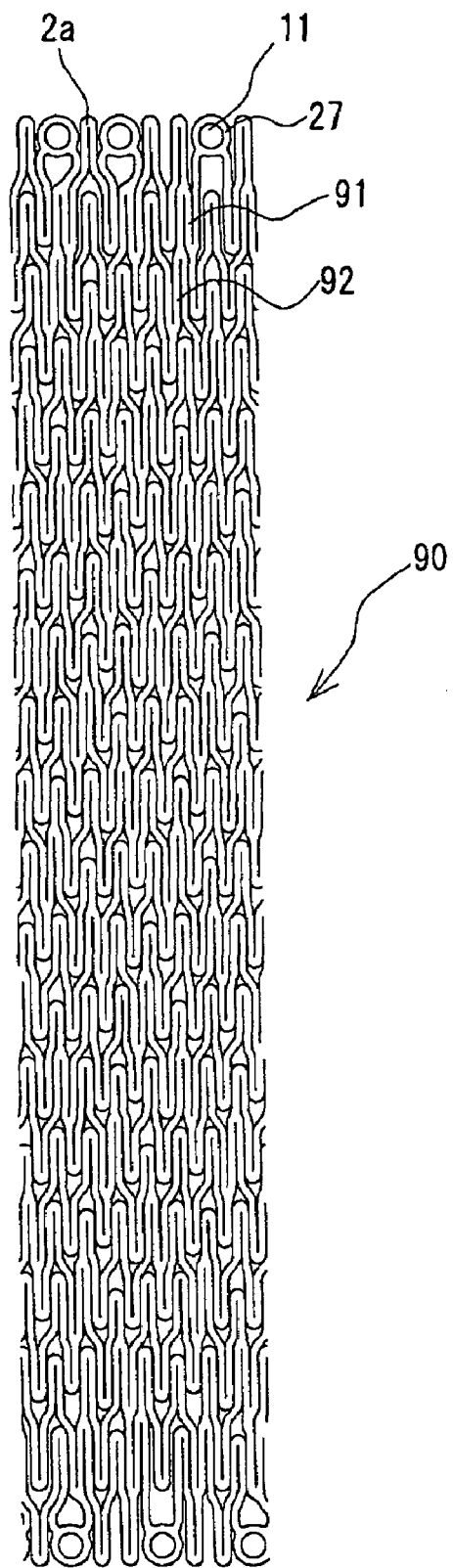
FIG. 21 is a development view showing the stent, shown in FIG. 20, when the stent is contracted.

The stent of the present invention may be formed as a stent 90 having a pattern as shown in FIGS. 20 and 21. FIG. 20 is a development view showing still another embodiment of the stent of the present invention. FIG. 21 is a development view showing the stent shown in FIG. 20, when the stent contracted.

The stent 90 has the same construction as that of the stent 1 except the number of the one-end side bent portions of one wavy annular member, the number of the other-end side bent portions thereof, the number of the sharing linear portions integrating the adjacent wavy annular members with each other, the arrangement form of the sharing linear portions, the orientation thereof, and the marker disposed at both ends of the stent.

The form of the stent 90 is similar to that of the above-described stent 50.

The number of the one-end side bent portions of one wavy annular member 2 of the stent 90 and that of the other-end side bent portions thereof are smaller than that of one wavy annular member 2 of the stent 1. More specifically, the number of the one-end side bent portions of one wavy annular member 2 of the stent 90 and that of the other-end side bent portions of one wavy annular member 2 thereof are eight respectively. In the axial direction of the stent 90, twenty-one wavy annular members 2 are disposed. In the stent 90, the adjacent two wavy annular members 2 are integrated with each other by two sharing linear portions 91 (first pattern sharing linear portion) or two sharing linear portions 92 (second pattern sharing linear portion). In the stent 90, the adjacent two wavy annular members 2 are integrated with each other by at least two sharing linear portions. The two sharing linear portions 91 are opposed to each other with respect to the axis of the stent 90. Similarly the two sharing linear portions 91 are opposed to each other with respect to the axis of the stent 90.

As shown in FIGS. 20 and 21, in the stent 90, the wavy annular member 2 disposed at both ends (upper and lower ends) of the stent and the adjacent wavy annular member 2 are integrated with each other with four sharing linear portions. At one end portion (upper end portion) of the stent 90, the above-described four sharing linear portions 91 are disposed substantially equiangularly with respect to the axis of the stent. Similarly, at the other end portion (lower end portion) of the stent 90, the above-described four sharing linear portions 92 are disposed substantially equiangularly with respect to the axis of the stent.

Because in the stent 90, a larger number of sharing linear portions are formed at both end portions of the stent than at other portions, the form or the configuration of both end portions of the stent is stable after the stent expands.

In the stent 90, the first pattern sharing linear portion 91 and the second pattern sharing linear portion 92 are disposed alternately with respect to the axial direction thereof. Further, the first pattern sharing linear portion 91 and the second pattern sharing linear portion 92 are disposed uncontinuously with each other in the axial direction of the stent 90. More specifically, the second pattern sharing linear portion 92 is shifted from the first pattern sharing linear portion 91 in the circumferential direction of the stent 90.

In the stent 90, the first pattern sharing linear portion 91 and the second pattern sharing linear portion 92 extend obliquely with respect to the axial direction of the stent and are different from each other in the orientation thereof.

In the stent 90, except both end portions thereof, one one-end side bent portion and one other-end side bent portion are disposed between the first pattern sharing linear portion 91 and the second pattern sharing linear portion 92 adjacent to the first pattern sharing linear portion 91 in the axial direction thereof. Two first pattern sharing linear portions 91 adjacent to each other in the axial direction of the stent and two second pattern sharing linear portions 92 adjacent to each other in the axial direction thereof are substantially equiangularly disposed with respect to the axis thereof. Thereby the stent 50 is capable of entirely displaying a substantially uniform expansive force.

As shown in FIG. 20, in the stent 90, the first pattern sharing linear portions 91 are spirally disposed in the axial direction thereof. Similarly the second pattern sharing linear portions 91 are spirally disposed in the axial direction thereof.

As shown in FIG. 20, the stent 90 has twenty-one wavy annular members arranged in the axial direction thereof. The first pattern sharing linear portions 91 are spirally disposed in the axial direction thereof. Similarly the second pattern sharing linear portions 92 are spirally disposed in the axial direction thereof. More specifically, the adjacent wavy annular members are connected with each other by two first pattern sharing linear portions 91. The first pattern sharing linear portions 91 are spirally disposed in the axial direction of the stent 90 to form two spirals. Each of the two spirals is composed of first pattern sharing linear portions 91. Similarly the adjacent wavy annular members (not connected by first pattern sharing linear portion 91) are connected with each other by two second pattern sharing linear portions 92. The second pattern sharing linear portions 92 are spirally disposed in the axial direction of the stent 90 to form two spirals. Each of the two spirals is constructed of five second pattern sharing linear portions 92.

As described above, the first pattern sharing linear portions 91 and the second pattern sharing linear portions 91 extend obliquely with respect to the axial direction of the stent 90 and are different from each other in the orientation thereof. It is preferable that the orientation of the first pattern sharing linear portion 91 and that of the second pattern sharing linear portion 92 are substantially symmetrical to each other with respect to the axis of the stent. Thereby the stent 90 is capable of entirely displaying a substantially uniform expansive force.

As shown in FIG. 20, one wavy annular member 2 of the stent 90 has a short linear portion 26 connecting the termination point 23 of the first pattern sharing linear portion 91 thereof and the apex 2a of the one-end side bent portion thereof to each other. The wavy annular member adjacent to the wavy annular member 2 having the short linear portion 26 has a short linear portion 25 connecting the start point 22 of the first pattern sharing linear portion 91 thereof and the apex 2b of the other-end side bent portion thereof to each other and a short linear portion connecting a termination point of the second pattern sharing linear portion 41 thereof and the apex of the one-end side bent portion thereof to each other.

As shown in FIGS. 20 and 21, the stent 90 has a contrast marker 11. It is favorable to dispose the contrast marker 11 at an end of the stent 80. It is more favorable to dispose the contrast marker 11 at both ends of the stent. More specifically, as shown in FIGS. 20 and 21, it is preferable to dispose a plurality of the markers 11 at both ends of the stent. The stent 90 of this embodiment has an opening 27 formed at an apex disposed at both ends of the stent. The marker 11 closing the opening 27 is fixed to the ends of the stent. The contrast marker is the same as that of the above-described stent 10.

As shown in FIGS. 20 and 21, an outer edge of the opening 27 is coincident with outer edges of other apexes disposed at the end (upper and lower ends) of the stent in the axial direction thereof. That is, in the stent 90, the outer edge of the opening 27 to which the marker is fixed is not projected outward from the outer edges of the other apexes disposed at the end of the stent. By making the outer edges of the stent coincident with one another in the axial direction of the stent, the stent can be securely pressed out, even though the stent is curved. In the stent 90, two leg portions are extended inward from a position located inward from an inner side of each opening 27 disposed at a bent portion, with the two leg portions spaced from each other at a predetermined interval. The two leg portions extended from the opening 27 are spaced from each other. That is, in the stent 90, the two leg portions extended from the opening 27 are not proximate to each other, unlike the leg portion of the stent 10 shown in FIG. 5. By spacing the two leg portions from each other at the predetermined interval, the configuration of the region in the vicinity of the marker-formed portion (opening 27) is stable. Therefore when a strong force is applied to the region in the vicinity of the marker-formed portion (opening 27), the stent is prevented from deforming and can be reliably pressed out.

The outer diameter, thickness, and length of the stent are different respectively in dependence on a portion where the stent is implanted. When the stent is expanded (when it is not contracted in its diameter and when it is restored to its original state), the outer diameter thereof is favorably in the range of 2.0 to 30 mm and more favorably in the range of 2.5 to 20 mm; the thickness thereof is favorably in the range of 0.04 to 1.0 mm and more favorably in the range of 0.06 to 0.5 mm; and the length thereof is favorably in the range of 10-150 mm and more favorably in the range of 15 to 100 mm. In the case of the stent to be implanted in the blood vessel the outer diameter thereof is favorably in the range of 2.0 to 14 mm and more favorably in the range of 2.5 to 12 mm; the thickness thereof is favorably in the range of 0.04 to 0.3 mm and more favorably in the range of 0.06 to 0.22 mm; and the length thereof is favorably in the range of 5-100 mm and more favorably in the range of 10 to 80 mm.

The stent is integrally and cylindrically made of the super-elastic alloy showing super-elasticity before and after the stent is inserted into the organism.

The super-elastic alloy can be preferably used as the super-elastic metal. Herein the super-elastic alloy means a so-called shape memory alloy that shows super-elasticity essentially at the temperature (in the vicinity of 37° C.) of the organism. The following super-elastic metals can be favorably used: A Ti—Ni alloy of 49-54 atomic percent of Ni, a Cu—Zn alloy of 38.5-41.5 wt % of Zn, a Cu—Zn—X alloy of 1-10 wt % of X (X=Be, Si, Sn, Al, Ga), and a Ni—Al alloy of 36-38 atomic percent of Al. The Ti—Ni alloy is most favorable. The mechanical characteristic of the Ti—Ni alloy can be appropriately changed by replacing a part of the Ti—Ni alloy with 0.01-10.0% of X to obtain a Ti—Ni—X alloy (X=Co, Fe, Mn, Cr, V, Al, Nb, W, B, Au, and Pd) or by replacing a part of the Ti—Ni alloy with 0.01-30.0 atomic percent of X to obtain a Ti—Ni—X alloy (X=Cu, Pb, Zr). Further the mechanical characteristic of the super-elastic alloy can be appropriately changed by selectively adopting a cold working ratio or/and the condition of final heat treatment.

In the case where the Ti—Ni—X alloy is used, it is also possible to change the mechanical characteristic of the super-elastic alloy appropriately by selectively adopting the cold working ratio or/and the condition of the final heat treatment. The buckling strength (yield stress when load is applied to stent) of the super-elastic alloy to be used is favorably in the range of 5-200 kg/mm$^2$ (22° C.) and more favorably in the range of 8-150 kg/mm$^2$. The restoring stress (yield stress when load is eliminated from stent) of the super-elastic alloy is favorably in the range of 3-180 kg/mm$^2$ (22° C.) and more favorably in the range of 5-130 kg/mm$^2$. The super-elasticity means that when a metal is deformed (bent, stretched, compressed) to a region in which it deforms plastically at a service temperature, it returns to its original configuration substantially without heating it after an applied load is eliminated.

The stent is formed by removing (for example, cutting, dissolving) a part of a pipe made of the super-elastic metal, not constituting the stent. Thereby the stent is obtained as an integral product. The pipe made of the super-elastic metal to be used to form the stent of the present invention can be produced by dissolving the super-elastic alloy such as the Ti—Ni alloy in an inactive gas atmosphere or a vacuum atmosphere to form an ingot thereof, polishing the ingot mechanically, forming a pipe having a large diameter by hot press and extrusion, repeating a drawing step and a heat treatment step to adjust the diameter and thickness of the pipe to a predetermined thickness and reduced diameter, and finally polishing the surface of the pipe chemically or physically. The pipe made of the super-elastic metal can be processed into the base material for the stent by a cutting work such as laser processing (for example, YAG laser), electrical discharge machining, chemical etching, cutting processing or in combination thereof.

The stent of the present invention may be coated with a material suitable for the organism on its inner surface, outer surface or inner and outer surfaces. As the material suitable for the organism, synthetic resin and metal suitable for the organism can be used. The following inactive metals are used to coat the surface of the stent gold by an electroplating method, stainless steel by an evaporation method, silicon carbide by a sputtering method, diamond-like carbon, plated titanium nitride, and plated gold. As the synthetic resin, the following thermoplastic resins or thermosetting resins can be used: polyolefin (for example, polyethylene, polypropylene, ethylene-propylene copolymer), polyvinyl chloride, ethylene-vinyl acetate copolymer, polyamide elastomer, polyurethane, polyester, fluorocarbon resin, silicone resin. It is preferable to use polyolefin, polyamide elastomer, polyester, polyurethane, silicone resin. A resin decomposable in the organism (polylactic acid, polyglycolic acid, polylactic acid-polyglycolic acid-copolymer) is also favorable. It is preferable that a film of the synthetic resin is soft such an extent as not to prevent a frame constituting the stent from being curved. The thickness of the film of the synthetic resin is favorably in the range of 3 to 300 μm and more favorably in the range of 5 to 100 μm.

As the method of thinly coating the surface of the stent with the synthetic resin, it is possible to use a method of inserting the stent into the melted synthetic resin or into the synthetic resin dissolved in a solution. It is also possible to use a chemical evaporation method of polymerizing a monomer over the surface of the pipe made of the super-elastic metal. In the case where the surface of the stent is coated very thinly with the synthetic resin, the use of a dilute solution or the chemical evaporation method is preferable. To improve the quality of the material suitable for the organism to a higher extent, the resinous film may be coated with an anti-thrombus material or the anti-thrombus material may be fixed to the resinous film. As the anti-thrombus material, known various resins can be used singly or as a mixture thereof. For example, polyhydroxyethyl methacrylate, a copolymer of hydroxyethyl methacrylate and styrene (for example, HEMA-St-HEMA block copolymer) can be preferably used.

The stents of the above-described embodiments are formed as a tube, have a diameter whose dimension is so set that it can be inserted into the lumen of the predetermined portion inside the organism, and can be expanded when a force spreading radially outwardly from the inside of the tube is applied thereto. That is, the stent may be the balloon expandable stent.

It is preferable that the material of the balloon expandable stent has a certain degree of compatibility with the organism. For example, it is possible to use stainless steel, tantalum or tantalum alloys, platinum or platinum alloys, gold or gold alloys, cobalt based alloys, a cobalt-chrome alloy, a titanium alloy, and a niobium alloy.

It is preferable to plate the stent with a noble metal such as gold and platinum after the stent is fabricated into a final shape. As the stainless steel, SUS 316L most corrosion-resistant can be preferably used.

It is preferable to anneal the stent after it is fabricated into the final shape. Annealing improves the flexibility and plasticity of the entire stent. Thereby the stent can be favorably implanted at a curved portion of a blood vessel. As compared with a non-annealed stent, the annealed stent has a lower force of restoring to an original state after it is expanded, and especially has a lower force of restoring to an original linear state when it is expanded at the curved portion of the blood vessel. This minimizes physical stimulation to the inner wall of the curved portion of the blood vessel, thus reducing the cause of a recurrence of stenosis. It is preferable to anneal the stent by heating it to 900 to 1200° C. in an inert gas atmosphere (e.g., a mixture gas of nitrogen and hydrogen) so that no oxide film is formed on the surface of the stent and then slowly cooling it.

The stent has a diameter favorably 0.8 to 1.8 mm and more favorably 0.9 to 1.6 mm in an unexpanded state. The stent has a length favorably 8 to 40 mm in an unexpanded state. It is preferable that each wavy annular members has a length of 8 to 25 mm. It is preferable that the length of each connection portion 3 is 20-100 mm.

The stent is shaped by removing portions other than a frame structure from a tube (more specifically, metal pipe). More specifically, the stent is formed by removing unnecessary portions from the metal pipe by an etching process, known as photo-fabrication, using masks and chemicals; cutting processing (for example, mechanical polishing, laser cutting processing), electric discharge machining, and in addition, by using the above-described methods in combination.

It is preferable to provide the stents of the above-described embodiments with a marker 11 as in the case of the stent 10 shown in FIG. 5. It is favorable to dispose the marker 11 at an end of each stent. It is more favorable to dispose the marker 11 at both ends of the stent. More specifically, as shown in FIG. 5, it is preferable to dispose a plurality of the markers 11 at both ends of the stent. The marker is as described above.

EXAMPLES

The examples of the stent of the present invention are described below.

Example 1

Cold working of a Ti—Ni alloy (51 atomic percent of Ni) was performed to prepare a super-elastic metal pipe having an outer diameter of about 1.9 mm, a thickness of about 0.25 mm, and a length of about 100 mm. The super-elastic metal pipe was set on a jig, provided with a rotary motor, which had a fastening mechanism for preventing the metal pipe from being off-centered. Thereafter the jig was set on an X table which can be numerically controlled. The X table and the rotary motor were connected to a personal computer. An output of the personal computer was inputted to a numerical controller of the X table and the rotary motor. A development drawing representing the stent having the structure shown in FIG. 3 was inputted to a design software of the personal computer storing. The X table and the rotary motor were driven in accordance with design data outputted from the personal computer.

The metal pipe was irradiated with laser beams to machine the metal pipe into a base material for the stent having a configuration whose development view is as shown in FIG. 3.

As the laser machining condition for the metal pipe, an average output and a drive speed were set to 5.5 W and 180 mm/minute respectively. The inner surface of the base material for the stent was machined.

Thereafter a core was inserted into the lumen of the base material for the stent to increase the diameter of the base material. The core had a diameter a little larger than that of the lumen. The base material for the stent was heat-treated, with the core remain inserted in the lumen. The configuration of the base material for the stent whose diameter was increased was stored. By the diameter-increasing step and the heat-treating step, the base material for the stent had a diameter a little (about 1 mm) larger than the original diameter thereof. It is preferable that the core is made of metal such as stainless steel and that the base material for the stent is heat-treated at 450 to 550° C. for 2 to 30 minutes. Another core having a diameter a little larger (about 2 mm larger than the increased diameter of the base material for the stent) than the above-described core was inserted into the lumen of the base material for the stent to increase the diameter of base material for the stent. Thereafter the base material for the stent was heat-treated. By repeating the diameter-increasing step and the heat-treating step until the base material for the stent attained the predetermined outer diameter, the base material for the stent as shown in FIG. 1 was prepared. Each time one heat-treating step is conducted, a chemical polishing step may be carried out as necessary.

After the base material for the stent shaped into the predetermined configuration went through blast treatment chemical polishing and electropolishing, a step of smoothening the surface of the base material for the stent and imparting metallic luster to the surface thereof was conducted.

The stent prepared in this manner had an outer diameter of about 8 mm, an entire length of about 45 mm, and a thickness of about 0.2 mm. The width of the linear portion of each wavy linear member was about 0.11 mm. The axial length of the wavy annular member was about 3 mm. The length of the sharing linear portion was about 1.6 mm. The length of the long linear portion was about 3.4 mm.

The stent had a sufficient expansive force. Further a strain did not concentrate on a connection portion.

Example 2

Cold working of a Ti—Ni alloy (51 atomic percent of Ni) was performed to prepare a super-elastic metal pipe having an outer diameter of about 1.9 mm, a thickness of about 0.25 mm, and a length of about 100 mm. The super-elastic metal pipe was set on a jig, provided with a rotary motor, which had a fastening mechanism for preventing the metal pipe from being off-centered. Thereafter the jig was set on an X table which can be numerically controlled. The X table and the rotary motor were connected to a personal computer. An output of the personal computer was inputted to a numerical controller of the X table and the rotary motor. A development drawing representing the stent having the structure shown in FIG. 11 was inputted to a design software of the personal computer storing. The X table and the rotary motor were driven in accordance with design data outputted from the personal computer.

The metal pipe was irradiated with laser beams to machine the metal pipe into base material for the stent having a configuration whose development view is as shown in FIG. 11.

As the laser machining condition for the metal pipe, an average output and a drive speed were set to 5.5 W and 180 mm/minute respectively. The inner surface of the base material for the stent was machined.

Thereafter a core was inserted into the lumen of the base material for the stent to increase the diameter of the base material. The core had a diameter a little larger than that of the lumen. The base material for the stent was heat-treated, with the core remain inserted in the lumen. The configuration of the base material for the stent whose diameter was increased was stored. By the diameter-increasing step and the heat-treating step, the base material for the stent had a diameter a little (about 1 mm) larger than the original diameter thereof. It is preferable that the core is made of metal such as stainless steel and that the base material for the stent is heat-treated at 450 to 550° C. for 2 to 30 minutes. Another core having a diameter a little larger (about 2 mm larger than the increased diameter of the base material for the stent) than the above-described core was inserted into the lumen of the base material for the stent to increase the diameter of base material for the stent. Thereafter the base material for the stent was heat-treated. By repeating the diameter-increasing step and the heat-treating step until the base material for the stent attained the predetermined outer diameter, the base material for the stent as shown in FIG. 9 was prepared. Each time one heat-treating step is conducted, a chemical polishing step may be carried out as necessary.

After the base material for the stent shaped into the predetermined configuration went through blast treatment chemical polishing, and electropolishing, a step of smoothening the surface of the base material for the stent and imparting metallic luster to the surface thereof was conducted.

The stent prepared in this manner had an outer diameter of about 8 mm, an entire length of about 45 mm, and a thickness of about 0.2 mm. The width of the linear portion of each wavy linear member was about 0.11 mm. The axial length of the wavy annular member was about 3 mm. The length of the sharing linear portion was about 1.6 mm.

The stent had a sufficient expansive force. Further a strain did not concentrate on a connection portion.

Example 3

Cold working of a Ti—Ni alloy (51 atomic percent of Ni) was performed to prepare a super-elastic metal pipe having an outer diameter of about 1.9 mm, a thickness of about 0.25 mm, and a length of about 100 mm. The super-elastic metal pipe was set on a jig, provided with a rotary motor, which had a fastening mechanism for preventing the metal pipe from being off-centered. Thereafter the jig was set on an X table which can be numerically controlled. The X table and the rotary motor were connected to a personal computer. An output of the personal computer was inputted to a numerical controller of the X table and the rotary motor. A development drawing representing the stent having the structure shown in FIG. 14 was inputted to a design software of the personal computer storing. The X table and the rotary motor were driven in accordance with design data outputted from the personal computer.

The metal pipe was irradiated with laser beams to machine the metal pipe into a base material for the stent having a configuration whose development view is as shown in FIG. 14.

As the laser machining condition for the metal pipe, an average output and a drive speed were set to 5.5 W and 180 mm/minute respectively. The inner surface of the base material for the stent was machined.

Thereafter a core was inserted into the lumen of the base material for the stent to increase the diameter of the base material. The core had a diameter a little larger than that of the lumen. The base material for the stent was heat-treated, with the core remain inserted in the lumen. The configuration of the base material for the stent whose diameter was increased was stored. By the diameter-increasing step and the heat-treating step, the base material for the stent had a diameter a little (about 1 mm) larger than the original diameter thereof. It is preferable that the core is made of metal such as stainless steel and that the base material for the stent is heat-treated at 450 to 550° C. for 2 to 30 minutes. Another core having a diameter a little larger (about 2 mm larger than the increased diameter of the base material for the stent) than the above-described core was inserted into the lumen of the base material for the stent to increase the diameter of base material for the stent. Thereafter the base material for the stent was heat-treated. By repeating the diameter-increasing step and the heat-treating step until the base material for the stent attained the predetermined outer diameter, the base material for the stent as shown in FIG. 12 was prepared. Each time one heat-treating step is conducted, a chemical polishing step may be carried out as necessary.

After the base material for the stent shaped into the predetermined configuration went through blast treatment, chemical polishing, and electropolishing, a step of smoothening the surface of the base material for the stent and imparting metallic luster to the surface thereof was conducted.

The stent prepared in this manner had an outer diameter of about 8 mm, an entire length of about 45 mm, and a thickness of about 0.2 mm. The width of the linear portion of each wavy linear member was about 0.11 mm. The axial length of the wavy annular member was about 3 mm. The length of the sharing linear portion was about 1.6 mm.

The stent had a sufficient expansive force. Further a strain did not concentrate on a connection portion.

Example 4

Cold working of a Ti—Ni alloy (51 atomic percent of Ni) was performed to prepare a super-elastic metal pipe having an outer diameter of about 1.9 mm, a thickness of about 0.25 mm, and a length of about 100 mm. The super-elastic metal pipe was set on a jig, provided with a rotary motor, which had a fastening mechanism for preventing the metal pipe from being off-centered. Thereafter the jig was set on an X table which can be numerically controlled. The X table and the rotary motor were connected to a personal computer. An output of the personal computer was inputted to a numerical controller of the X table and the rotary motor. A development drawing representing the stent having the structure shown in FIG. 17 was inputted to a design software of the personal computer storing. The X table and the rotary motor were driven in accordance with design data outputted from the personal computer.

The metal pipe was irradiated with laser beams to machine the metal pipe into a base material for the stent having a configuration whose development view is as shown in FIG. 17.

As the laser machining condition for the metal pipe, an average output and a drive speed were set to 5.5 W and 180 mm/minute respectively. The inner surface of the base material for the stent was machined.

Thereafter a core was inserted into the lumen of the base material for the stent to increase the diameter of the base material. The core had a diameter a little larger than that of the lumen. The base material for the stent was beat-treated, with the core remain inserted in the lumen. The configuration of the base material for the stent whose diameter was increased was stored. By the diameter-increasing step and the heat-treating step, the base material for the stent had a diameter a little (about 1 mm) larger than the original diameter thereof. It is preferable that the core is made of metal such as stainless steel and that the base material for the stent is heat-treated at 450 to 550° C. for 2 to 30 minutes. Another core having a diameter a little larger (about 2 mm larger than the increased diameter of the base material for the stent) than the above-described core was inserted into the lumen of the base material for the stent to increase the diameter of base material for the stent. Thereafter the base material for the stent was heat-treated. By repeating the diameter-increasing step and the heat-treating step until the base material for the stent attained the predetermined outer diameter, the base material for the stent as shown in FIG. 15 was prepared. Each time one heat-treating step is conducted, a chemical polishing step may be carried out as necessary.

After the base material for the stent shaped into the predetermined configuration went through blast treatment chemical polishing, and electropolishing, a step of smoothening the surface of the base material for the stent and imparting metallic luster to the surface thereof was conducted.

The stent prepared in this manner had an outer diameter of about 8 mm, an entire length of about 45 mm, and a thickness of about 0.2 mm. The width of the linear portion of each wavy linear member was about 0.11 mm. The axial length of the wavy annular member was about 3 mm. The length of the sharing linear portion was about 1.6 mm.

The stent had a sufficient expansive force. Further a strain did not concentrate on a connection portion.

EXPERIMENT

The stent is implanted at various portions of lumens of an organism. Thus functions of the stent are different from one another in dependence on portions of the lumens. It is preferable that the stent has a comparatively high resistance to axial expansion and contraction thereof and is strong when the stent is implanted in the carotid artery and the renal artery. This is because these blood vessels expand and contract to a low extent for a movement of the organism. Therefore it is preferable to use the stent which expands and contracts to a low extent and holds the blood vessels firmly.

The superficial femoral artery and the popliteal artery expand and contract to a high extent for a movement of the organism. Further in many cases, because a lesion in the lower limbs is long, it is necessary to implant a long stent in these blood vessels. In this case, the stent is demanded to have a comparatively low resistance to axial expansion and contraction thereof and be axially flexible. As a result of energetic researches of the present inventors, they have developed stents having approximately the same constructions but different resistances (flexibilities) to the axial expansion and contraction thereof.

The resistance of each of the stents of the examples 1 through 4 to the axial expansion and contraction thereof was measured. More specifically, the resistance of each stent having an outer diameter of 8 mm and a length of 45 mm was measured when it was contracted by 20% of the remaining length of 30 mm, namely, by 6 mm, with each stent held at a position thereof spaced at 7.5 mm from both ends thereof.

TABLE 1

| | Stent | | | |
|---|---|---|---|---|
| | Example 1 | Example 2 | Example 3 | Example 4 |
| Resistance | 43.5 gf | 11.5 gf | 18.3 gf | 17.2 gf |

The results indicate that the stent of the example 1 had a comparatively high resistance to the axial expansion and contraction thereof and held blood vessels firmly. Thus the stent of the example 1 is suitable for being implanted in the carotid artery, the renal artery, and the like. The reason the resistance of the stent of the example 1 to the axial expansion and contraction thereof is comparatively high is because the long linear portion 24 is spirally continuous through two bent portions, namely, through the start point 22 and the termination point 23.

The stent of the examples 2 through 4 had a resistance not more than the half of that of the stent of the example 1 to the axial expansion and contraction thereof. Thus these stents are suitable for being implanted in the arteries of the lower limbs such as the superficial femoral artery, the popliteal artery, and the like. The reason the resistance of these stents to the axial expansion and contraction thereof is comparatively low is because they do not have a clear long linear portion and because the sharing linear portions are uncontinuous. The stent of the example 2 has only two sharing linear portions spaced by 180 degrees (opposed to each other with respect to the axis of the stent). Therefore the stent of the example 2 showed the lowest resistance.

The stent of the present invention to be implanted in the organism includes a plurality of the wavy annular members arranged in the axial direction thereof. In this construction, each of the wavy annular members has a plurality of the one-end side bent portions each having the apex at the one-end side of the stent in the axial direction thereof and a plurality of other-end side bent portions each having the apex at the other-end side of the stent in the axial direction thereof. In the wavy annular members disposed adjacently to each other in the axial direction of the stent, the wavy annular member disposed at the one-end side of the stent in the axial direction thereof has the sharing linear portion having the start point at the apex of one of the other-end side bent portions thereof or in the vicinity of the apex and the termination point between the apex of the other-end side bent portion thereof and the apex of one of the one-end side bent portions thereof. The sharing linear portion integrates the adjacent wavy annular members with each other. The stent does not substantially display an expansive force or a connection portion having a possibility of adversely affecting the performance of the stent when the stent is curved. Further the adjacent wavy linear members are integrated with each other with the sharing linear portion. Therefore the stent has a sufficient and uniform expansive force.

What is claimed is:

1. A stent comprising: a plurality of wavy annular members arranged in an axial direction thereof,
   wherein each of said wavy annular members has a plurality of one-end side bent portions each having an apex at a one-end side of said stent in said axial direction thereof and a plurality of other-end side bent portions each having an apex at an other-end side of said stent in said axial direction thereof; and
   in said wavy annular members disposed adjacently to each other in said axial direction of said stent, said wavy annular member disposed at said one-end side of said stent in said axial direction thereof has a sharing linear portion having a start point at or in the vicinity of said apex of one of said other-end side bent portions of said wavy annular member disposed at said one-end side of said stent, and a termination point between said apex of said other-end side bent portion of said wavy annular member disposed at said one-end side of said stent and said apex of one of said one-end side bent portions of said wavy annular member disposed at said one-end side of said stent, wherein said wavy annular member disposed at said one-end side of said stent comprises both the start point and the termination point of said sharing linear portion;
   said stent having a plurality of said sharing linear portions integrating said adjacent wavy annular members with each other;
   wherein said sharing linear portions comprises first pattern sharing linear portions extending obliquely with respect to said axial direction of said stent and second pattern sharing linear portions extending obliquely with respect to said axial direction of said stent in a direction different from the direction in which said first pattern sharing linear portions extend, and wherein said first pattern sharing linear portions and said second pattern sharing linear portions are disposed alternately in said axial direction of said stent;
   wherein said wavy annular member has a short linear portion connecting said start point of said sharing linear portion thereof and the apex of said other-end side bent portion thereof to each other; and
   wherein said short linear portions each connecting said start point of said sharing linear portion and said apex of said other-end side bent portion to each other are formed not continuously in said axial direction of said stent, but said short linear portions are formed substantially straight.

2. A stent according to claim 1, wherein said stent has a bifurcating portion formed by said start point of said sharing linear portion and a bifurcating portion formed by said termination point of said sharing linear portion.

3. A stent according to claim 1, wherein said wavy annular member has a short linear portion connecting said termination point of said sharing linear portion thereof and the apex of said one-end side bent portion thereof to each other.

4. A stent according to claim 1, wherein each of said wavy annular members has a big wavy portion forming a projected one-end side apex projected closer to said one-end of said stent than said apexes of other one-end side bent portions and a projected other-end side apex projected closer to said other-end of said stent than said apexes of other other-end side bent portions.

5. A stent according to claim 4, wherein a linear portion disposed between said projected one-end side apex of said big wavy portion and said projected other-end side apex thereof form a long linear portion.

6. A stent according to claim 1, wherein said wavy annular member has a long linear portion connecting a termination point of said sharing linear portion thereof and an apex of said other-end side bent portion thereof to each other.

7. A stent according to claim 1, wherein a plurality of sharing linear portions is formed between said wavy annular members adjacent to each other in said axial direction of said stent.

8. A stent according to claim 1, wherein a plurality of sharing linear portions is formed between said wavy annular members adjacent to each other in said axial direction of said stent; and a plurality of said sharing linear portions is formed oppositely to each other or substantially equiangularly with respect to said axial direction of said stent.

9. A stent according to claim 1, wherein said wavy annular member has a plurality of big wavy portions.

10. A stent according to claim 1, wherein said wavy annular member has a plurality of big wavy portions; and a plurality of said big wavy portions is formed oppositely to each other or substantially equiangularly with respect to said axial direction of said stent.

11. A stent according to claim 1, wherein said apex of each of said one-end side bent portions of each wavy annular member penetrates into a space formed between said apexes of said adjacent other-end side bent portions of one of said adjacent wavy annular members; and said apex of each of said other-end side bent portions of each wavy annular member penetrates into a space formed between said apexes of said adjacent one-end side bent portions of said other of said adjacent wavy annular members.

12. A stent according to claim 1, wherein said stent is a self-expandable stent which is formed substantially cylindrically, decreased in a diameter thereof when said stent is inserted into an organism, and is capable of returning to a configuration before said diameter of said stent is decreased when said stent is implanted in said organism.

13. A stent according to claim 1, wherein said stent is formed as a tube, has a diameter whose dimension is so set that said stent can be inserted into a lumen inside an organism, and can be expanded when a force spreading radially outwardly from an inside of said tube is applied thereto.

14. A stent according to claim 1, wherein said second pattern sharing linear portion is shifted from said first pattern sharing linear portion in a circumferential direction of said stent.

15. A stent according to claim 1, wherein a coupling portion for coupling a wavy annular member disposed at both ends of said stent and a wavy annular member adjacent thereto to each other.

16. A stent according to claim 1, wherein a larger number of sharing linear portions are formed between a wavy annular member disposed at both ends of said stent and a wavy annular member adjacent thereto than between adjacent wavy annular members disposed at other portions of said stent.

17. A stent according to claim 1, comprising a contrast marker provided at an end of said stent, wherein an end of said contrast marker is not projected beyond said end of said stent.

18. A stent according to claim 1, comprising an opening formed at an apex disposed at one end of the stent and for fixing said contrast maker has two leg portions extending toward an other end of the stent, and said the two leg portions are spaced from each other and substantially parallel.

19. A stent according to claim 1, wherein said termination point of said first pattern sharing linear portion is connected to a first linear portion of said wavy annular member, said termination point of said second pattern sharing linear portion is connected to a second linear portion of said wavy annular member, and said first and second linear portions are connected via a third linear portion of said wavy annular member.

20. A stent according to claim 19, wherein said first linear portion is not directly connected to said second pattern sharing linear portion, and said second linear portion is not directly connected to the first pattern sharing linear portion.

21. A stent according to claim 1, wherein all of the wavy annular members except a wavy annular member located at one end of the stent have a short linear portion connecting said start point of said sharing linear portion thereof and the apex of said other-end side bent portion thereof to each other.

22. A stent comprising: a plurality of wavy annular members arranged in an axial direction thereof,
wherein each of said wavy annular members has a plurality of one-end side bent portions each having an apex at a one-end side of said stent in said axial direction thereof and a plurality of other-end side bent portions each having an apex at an other-end side of said stent in said axial direction thereof; and
in said wavy annular members disposed adjacently to each other in said axial direction of said stent, said wavy annular member disposed at said one-end side of said stent in said axial direction thereof has a sharing linear portion having a start point at or in the vicinity of said apex of one of said other-end side bent portions of said wavy annular member disposed at said one-end side of said stent, and a termination point between said apex of said other-end side bent portion of said wavy annular member disposed at said one-end side of said stent and said apex of one of said one-end side bent portions of said wavy annular member disposed at said one-end side of said stent, wherein said wavy annular member disposed at said one-end side of said stent comprises both the start point and the termination point of said sharing linear portion;
said stent having a plurality of said sharing linear portions integrating said adjacent wavy annular members with each other;
wherein said sharing linear portions comprises first pattern sharing linear portions extending obliquely with respect to said axial direction of said stent and second pattern sharing linear portions extending obliquely with respect to said axial direction of said stent in a direction different from the direction in which said first pattern sharing linear portions extend, and wherein said first pattern sharing linear portions and said second pattern sharing linear portions are disposed alternately in said axial direction of said stent;
wherein said wavy annular member has a short linear portion connecting said termination point of said sharing linear portion thereof and the apex of said one-end side bent portion thereof to each other; and
wherein said short linear portions each connecting said termination point of said sharing linear portion and said apex of said one-end side bent portion to each other are formed not continuously in said axial direction of said stent, but said short linear portions are formed substantially straight.

23. A stent according to claim 22, wherein all of the wavy annular members except a wavy annular member located at one end of the stent have a short linear portion connecting said start point of said sharing linear portion thereof and the apex of said other-end side bent portion thereof to each other.

* * * * *

UNITED STATES PATENT AND TRADEMARK OFFICE
CERTIFICATE OF CORRECTION

PATENT NO. : 7,618,445 B2
APPLICATION NO. : 11/392490
DATED : November 17, 2009
INVENTOR(S) : Moriuchi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 409 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,618,445 B2 | |
| APPLICATION NO. | : 11/392490 | |
| DATED | : November 17, 2009 | |
| INVENTOR(S) | : Yousuke Moriuchi et al. | |

It is certified that error appears in the above-identified patent and that said Letters Patent is hereby corrected as shown below:

In column 1, line 7, insert --,-- after "duct".
In column 1, line 61, insert --,-- after "stent".
In column 4, line 23, insert --,-- after "embodiment".
In column 4, line 30, insert --,-- after "embodiment".
In column 8, line 19, change "4" to --41--.
In column 8, line 54, change "dearly" to --clearly--.
In column 13, line 27, insert --,-- after "stent".
In column 13, line 36, insert --,-- after "stent".
In column 22, line 32, insert --,-- after "treatment".

Signed and Sealed this
Twentieth Day of December, 2011

David J. Kappos
*Director of the United States Patent and Trademark Office*